(12) United States Patent
Fisher et al.

(10) Patent No.: US 10,597,728 B2
(45) Date of Patent: Mar. 24, 2020

(54) METHYLATION SITE REGULATING EXPRESSION OF MDA-9/SYNTENIN

(71) Applicant: VIRGINIA COMMONWEALTH UNIVERSITY, Richmond, VA (US)

(72) Inventors: Paul B. Fisher, Richmond, VA (US); Manny Bacolod, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 18 days.

(21) Appl. No.: 15/574,283

(22) PCT Filed: May 13, 2016

(86) PCT No.: PCT/US2016/032431
§ 371 (c)(1),
(2) Date: Nov. 15, 2017

(87) PCT Pub. No.: WO2016/187030
PCT Pub. Date: Nov. 24, 2016

(65) Prior Publication Data
US 2018/0135130 A1 May 17, 2018

Related U.S. Application Data

(60) Provisional application No. 62/162,213, filed on May 15, 2015.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 2007/0231797 A1* | 10/2007 | Fan | C12Q 1/6827 435/6.12 |
| 2010/0143929 A1 | 6/2010 | Levenson et al. | |
| 2011/0104695 A1 | 5/2011 | Lofton-Day et al. | |
| 2012/0178634 A1 | 7/2012 | Sakai et al. | |
| 2014/0274767 A1 | 9/2014 | Yegnasubramanian et al. | |

OTHER PUBLICATIONS

Baysan et al PLoS One 9(4): e94045 (Apr. 11, 2014).*
Bacolod et al., "Examination of Epigenetic and other Molecular Factors Associated with mda-9/Syntenin Dysregulation in Cancer Through Integrated Analyses of Public Genomic Datasets", Adv Cancer Res, May 23, 2015, pp. 49-121, vol. 127.

* cited by examiner

*Primary Examiner* — Carla J Myers
(74) *Attorney, Agent, or Firm* — W & C IP

(57) ABSTRACT

Methods of prognosing the outcome of cancer and/or cancer treatment are provided. The methods involve quantitating the level of methylation at a site that regulates expression of the mda-9/Syntenin gene, site cg17197774. High levels of methylation indicate a good prognosis whereas low levels of methylation indicate a poor prognosis and determination of these levels permits risk stratification of patients with cancer.

11 Claims, 21 Drawing Sheets
Specification includes a Sequence Listing.

| Grp | No. Deceased | No. Alive |
|---|---|---|
| L | 26 | 98 |
| M | 72 | 52 |
| H | 75 | 49 |

Log rank/Wilcoxon tests: *p < 0.0001*

Melanoma *(Ab HPA023840)*

Glioma *(Ab HPA023840)*

Core Enrichment Genes: *IL2RA, IL5RA, IL7R, IL13RA2, IL2RB, IL1R, IL2RG, CSF2RB, IL10RA, CXCR2, IL4R, IL15RA, IL12RB1, IL10RB*

Core Enrichment Genes: *CFB, CFD, C6, C7, C1S, C1R, C2, C1QA, C1QB, C3, C1QC*

Core Enrichment Genes: MMP1, IGFBP2, IGFBP4, IGFBP3, PAPPA2, IGFBP5, CTSG, IGFBP6, PAPPA, IGFBP1, MMP2

Core Enrichment Genes: PLA2G2A, SH2D2A, PLA2G5, VEGFA, RAC2, PTGS2, HSPB1, PIK3CG, PIK3R5, PLA2G4A, SPHK1, MAPK13, PLA2G2D, NFATC2

METHYLATION SITE REGULATING EXPRESSION OF MDA-9/SYNTENIN

CROSS-REFERENCE TO RELATED APPLICATIONS

This application claims benefit of U.S. provisional patent application 62/162,213, filed May 15, 2015, the complete contents of which is hereby incorporated by reference.

STATEMENT OF FEDERALLY SPONSORED RESEARCH AND DEVELOPMENT

This invention was made with government support under RO1 CA134721 awarded by the National Institutes of Health. The United States government has certain rights in the invention.

SEQUENCE LISTING

This application includes as the Sequence Listing the complete contents of the accompanying .txt file "Sequence.txt", created May 10, 2016, containing 4.096 bytes, hereby incorporated by reference.

BACKGROUND OF THE INVENTION

Field of the Invention

The invention generally relates to methods of prognosing the outcome of cancer and/or the efficacy of cancer treatment. In particular, the invention provides methods for quantitating the level of methylation at site cg17197774, which regulates expression of the mda-9/Syntenin gene. Low levels of methylation indicate higher grade tumors, increased metastatic potential and a poorer prognosis for recovery, while higher levels of methylation indicate a good prognosis.

Background mda-9/Syntenin (Melanoma differentiation-associated gene 9), a gene located in chromosome 8, codes for a 33 KDa protein known to mediate a wide array of signaling pathways and cellular functions, including protein cell surface localization, and cell adhesion. mda-9 is known to play crucial roles in cancer progression, particularly during the invasion/metastasis stage. In melanoma, it acts as a positive regulator of metastasis, which is partially attributed to its interaction with c-Src, which eventually leads to the activation of the transcription factor NF-κB. These changes induce an increase in the transcription of matrix metalloproteinases (MMPs), necessary for the degradation of extracellular matrix during invasion (8). MDA-9s invasion-promoting property is also evident in glioma. The over-expression of mda-9 may lead to activation of c-Src, p38 MAPK and NF-κB, and eventually the elevated expression of MMP2 and secretion of interleukin-8 (IL-8). mda-9 is also over-expressed in metastatic, as well as ER-negative breast cancer. MDA-9's regulation of cell migration has also been demonstrated in colorectal cancer, a cancer type in which poor clinical outcome is associated with elevated expression of this gene.

Despite the wealth of mda-9-related knowledge described above, there is still much to learn regarding the gene and its involvement in cancer progression. One area that has not heretofore been investigated is how genetic and epigenetic factors contribute to its elevated expression during cancer progression, and uses of that knowledge to predict clinical outcomes, select suitable courses of treatment and monitor the efficacy of cancer treatment.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Described herein are comprehensive sets of analyses which identify the epigenetic factors involved in mda-9 regulation, and the application of those discoveries to molecular diagnostic tools for clinical applications in the diagnosis and treatment of cancer. According to some aspects, the detection of the level of methylation at site cg17197774, which regulates expression of the mda-9/Syntenin gene, is combined with other approaches (e.g. other markers for cancer development, progression and response to therapy) to enhance diagnostic and prognostic outcomes in normal and cancer patients. The other approaches include but are not limited to detection of expression of MDA-9/Syntenin regulated downstream gene expression (e.g. through RNAseq analysis), as well as detection of serum or other fluid biomarkers for cancer and metastasis. Using the mda-9/Syntenin methylation signature with liquid biopsy with isolated CTCs significantly enhances the sensitivity and prognostic ability of cancer prognostic assays.

The level of methylation at site cg17197774, which regulates expression of the mda-9/Syntenin gene, has been shown to be inversely correlated with the severity of the cancer (e.g. metastatic potential, grade of a tumor, likelihood of survival, etc.). Thus, cg17197774 methylation levels can be measured and used to diagnose and/or confirm a diagnosis of cancer, to identify tumor grade and/or metastatic status or potential, to predict the likely outcome of the course of the disease, to inform decisions regarding which treatment options should be pursued, to treat a subject with cancer, and also to monitor the efficacy of treatment and thus aid in a decision of whether to continue, discontinue, change, etc. a treatment regimen. In general, low levels of methylation indicate the presence of a highgrade tumor, increased metastatic potential and a poorer prognosis for recovery, and usually aggressive therapy is recommended. In contrast, a high level of methylation is indicative of a lower grade of tumor with a lower metastatic potential and a better prognosis for recovery, and less aggressive therapy may be recommended. For example, if a low level of methylation is detected, a trained medical practitioner is likely to recommend that the patient undergo aggressive therapy, e.g. surgery, high dose radiation and/or chemotherapy, lengthy courses of radiation and/or chemotherapy, etc. In contrast, if high levels of methylation are detected, more moderate approaches to treatment might be pursued, e.g. only one of surgery, radiation and chemotherapy, an attenuated course of radiation and/or chemotherapy, or even a period of "watchful waiting" during which the status of the tumor is monitored without treatment.

In some aspects, determination of the leve of methylation at cg17197774 is performed together with one or more of: RNA (e.g. mRNA) detection and sequencing from the tumor cells in bodily fluids, detection of the expression of downstream marker genes activated by MDA-9/Syntenin (which are also indicators of and/or correlated with lower promoter methylation), protein biomarker analysis of the bodily fluid indicating expression of MDA-9/Syntenin protein, etc. Such an analysis provides a complete picture and approach for diagnosing, stratifying, defining therapeutic response, monitoring dormancy, tumor progression, tumor activation, etc.

It is an object of this invention to provide methods of prognosing cancer in a subject in need thereof. The methods comprise i) measuring a level of CpG methylation at cg17197774 in a tumor sample from the subject, and ii) based on the level of CpG methylation measured in step i), assigning a poor prognosis to the subject if a low level of CpG methylation is detected; or assigning a good prognosis to the subject if a high level of CpG methylation is detected. In some aspects, the methods also comprise measuring, in the tumor sample form the subject, one or more of i) a level of CpG methylation at cg17197774; ii) a level of MDA-9/Syntenin protein expression; iii) a level of expression of downstream marker genes activated by MDA-9/Syntenin, and iv) a copy number of mda-9/Syntenin.

The invention also provides methods of treating a subject for cancer comprising. measuring a level of CpG methylation at cg17197774 in a tumor sample from the subject, wherein a low level of CpG methylation indicates a poor prognosis and a high level of CpG methylation indicates a good prognosis, and if the subject is found to have a poor prognosis, then treating the subject with an aggressive treatment, and if the subject is found to have a good prognosis, then treating the subject with no treatment of with a moderate treatment. In some aspects, the method also include measuring, in the a tumor sample form the subject, one or more of i) a level of CpG methylation at cg17197774; ii) a level of MDA-9/Syntenin protein expression; iii) a level of expression of downstream marker genes activated by MSA-9/syntenin, and iv) a copy number of mda-9/Syntenin. In some aspects, the aggressive treatment includes at least two, three or four of: surgical debulking, aggressive chemotherapy, aggressive radiation therapy, and adjunct immunotherapy. In some aspects, the moderate treatment includes one or more of: monitoring the tumor without treatment, surgical debulking, a short or moderate course of chemotherapy, and limited or moderate radiation therapy.

The invention also provides methods of monitoring cancer treatment in a subject in need thereof, comprising i) prior to beginning the cancer treatment, measuring a pre-treatment level of CpG methylation at site cg17197774 in a tumor sample from the subject, ii) administering the cancer treatment to the subject, and, after the step of administering, iii) measuring a post-treatment level of CpG methylation at cg17197774; and if the post-treatment level of CpG methylation is higher than the pre-treatment level of CpG methylation, then concluding that the cancer treatment is effective and maintaining or discontinuing the treatment; or if the post-treatment level of CpG methylation is the same as or lower than the pre-treatment level of CpG methylation, then concluding that the cancer treatment is not effective and providing a different cancer treatment to the subject. In some aspects, the methods further comprise measuring, in a tumor sample form the subject, one or more of i) a level of CpG methylation at cg17197774; ii) a level of MDA-9/Syntenin protein expression; iii) a level of expression of downstream marker genes activated by MDA-9/Syntenin, and iv) a copy number of mda-9/Syntenin. In some aspects, the methods also comprise repeating steps ii) and iii) a plurality of times during a course of treatment and/or after the course of treatment is finished.

The invention also provides methods of determining whether a tumor is dormant or active in a subject in need thereof, comprising i) measuring a level of CpG methylation at cg17197774 in a tumor sample from the subject, ii) based on the level of CpG methylation measured in step i), concluding that the tumor is dormant if a high level of CpG methylation is detected; or concluding that the tumor is active if a low level of CpG methylation is detected. For example, an active tumor may be actively metastasizing and/or may be a highly invasive tumor. In some aspects, the methods further comprise measuring, in the tumor sample form the subject, one or more of i) a level of CpG methylation at cg17197774; ii) a level of MDA-9/Syntenin protein expression; iii) a level of expression of downstream marker genes activated by MDA-9/Syntenin, and iv) a copy number of mda-9/Syntenin.

In some aspects, for any of the above methods, the low level of CpG methylation and the high level of CpG methylation are established by comparison to one or more of: a reference value from a control population of subjects with a high grade tumor prior to treatment; a reference value from a control population of subjects with a low grade tumor prior to treatment; a reference value from a control population of cancer-free subjects who have never been diagnosed with cancer; a reference value from a control population of subjects who have been diagnosed with and are being treated for cancer; a reference value from a control population of cancer-free subjects who have previously been successfully treated for cancer; a reference value from a control population of subjects diagnosed with metastatic cancer, and a reference value from normal or tumor tissue from the subject.

In some aspects, for any of the above methods the cancer (or the tumor) is glioma, prostate cancer, melanoma, liver hepatocellular carcinoma, kidney papillary carcinoma and colon adenocarcinoma.

In some aspects, for any of the above methods the tumor sample is a liquid biopsy.

In some aspects, for any of the above methods, the downstream marker genes are IGFBP-2 and urokinase-type plasminogen activator (uPA).

The invention also provides methods of assessing a cancerous tumor, comprising i) obtaining a tumor sample from a subject, and ii) measuring a level of CpG methylation of cg17197774 in the tumor sample.

DETAILED DESCRIPTION

Figure 1A:
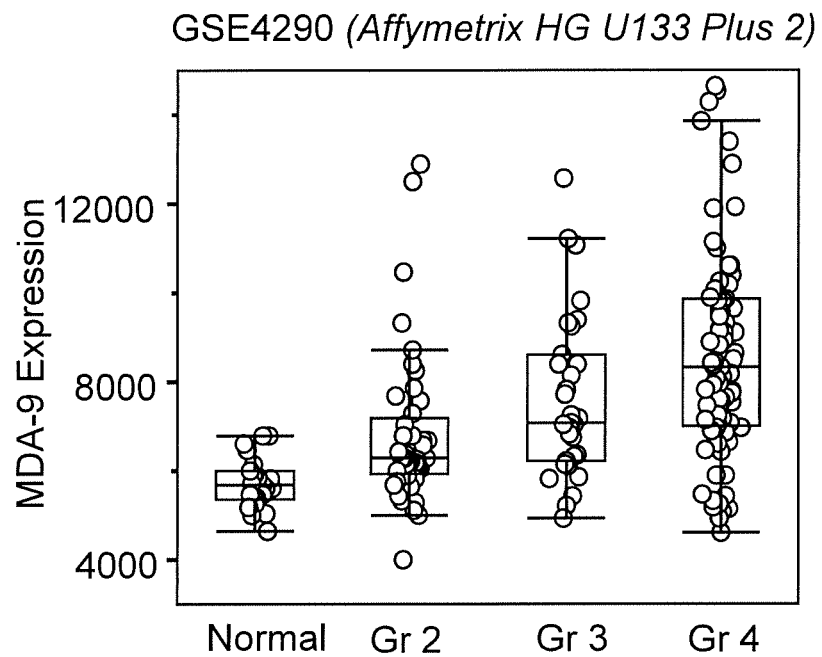
FIG. 1A-D. A. The progressive increase in the expression level of mda-9/Syntenin in glioma as observed in A, the GEO dataset GSE4290 and B, the TCGA Glioma dataset. C, overall survival of glioma patients, grouped according to MDA-9 expression level; D, data is tabular form.

Provided herein are methods that include but are not limited to: diagnosing cancer, confirming diagnoses of cancer, determining a grade and/or metastatic status or potential of a tumor, prognosing the likely course of disease in a subject with cancer, selecting a suitable treatment strategy for a subject with cancer, treating a subject with a suitable treatment strategy, patient stratification, and monitoring the efficacy of a treatment strategy, including methods of deciding when and/or whether to cease or change treatment.

The methods involve measuring a level of methylation of the site cg17197774 in a biological sample from a subject of interest, e.g. a subject who has been diagnosed with cancer, or has been deemed likely to have cancer, or to be at high risk of developing cancer (e.g. due to a genetic predisposition to cancer, due to exposure to carcinogens, etc.). Alternatively, the methods described herein may be used as part of routine health screening of subjects who are apparently healthy, in order to detect as yet asymptomatic cancer or cancer metastasis. For example, when cancer cells are isolated from patients (in some bodily fluid, such as liquid biopsy from blood) with presumed or possible localized tumors that do not however show any symptoms, screening is possible. This approach, which involves performing single cell sequencing, makes it possible to know the background of cells, i.e. if it originated from a tumor or from healthy tissue.

Such risk-stratified care management (RSCM) is a process of assigning a health risk status to a patient, and using the patient's risk status to direct and improve care. The goal of RSCM is to help patients achieve the best health and quality of life possible by preventing chronic disease, stabilizing current chronic conditions, and preventing acceleration to higher-risk categories by separating patient populations into high-risk, low-risk, and optionally medium and/or rising-risk groups.

As used herein, a "biological sample" encompasses a tumor tissue sample (e.g. a biopsy sample) from a primary tumor, from a metastatic tumor, form tissue surrounding a tumor, lymph nodes located at the closest proximity of the tumor, cells in blood samples. known as circulating tumor cells. etc. The term encompasses pieces or slices of tissue that have been removed including following a surgical tumor resection or following the collection of a tissue sample for biopsy, and/or cells obtained from a tumor. Alternatively, in some aspects, the biological sample is a sample of circulating cells, i.e. a "liquid biopsy". Samples that contain suitable circulating cells include but are not limited to: blood, plasma, serum, urine, saliva, sputum, breast milk, etc. In such samples, methylation can be measured in cells and/or other circulating material, including but not limited to: circulating tumor cells, exosomes, circulating or cell-free DNA, etc. Generally, in order to measure DNA methylation, DNA is extracted from the sample and treated as necessary for a particular measurement technique.

Those of skill in the art are aware of methods of detecting and quantitating (measuring) the level of DNA methylation at a site of interest such as cg17197774. Exemplary methods include but are not limited to: pyrosequencing, high-throughput quantitative methylation assays that utilizes fluorescence-based real-time PCR technology, quantitative methylation specific PCR (QMSP) on bisulfite modified nucleic acid, microarray-based CpG methylation quantitation, etc. For bisulfite sequencing sodium bisulfite converts unmethylated cytosines to uracils (which after PCR are converted to thymines), while leaving methylated cytosines unconverted. By mapping bisulfite treated DNA back to the original reference genome, the methylation state of individual cytosines is determined.

In some aspects, the romoter methylation status is detected in cells isolated from blood and the analysis is conducted using a multiplex sequencing platform such as a Roche 454 sequencing platform, an Illumina multiplex sequencing platform, a NuGEN Encore 384 multiplex platform, etc. Further, in some aspects, the methylation status is analysed by non-methylation-specific PCR based methods, methylation-based methods or microarray-based methods, e.g. Epityper or Methylight (qPCR) assays.

In some aspects, the level of methylation that is measured is expressed as a relative methylation score (which may be termed a "z score" or by some other nomenclature), a relative expression that is determined in comparison to reference values e.g. from a database. Generally, reference values for at least normal tissue, primary tumor tissue, and metastatic tumor tissue, are provided. A normal reference may be established based on tissue from healthy subjects, and/or from normal tissue from the patient him/herself. The reference values may also be calculated or adapted to individual cancer types. In some aspects, the methylation status is calculated for a given sample, without the need of a control. Many existing assays are capable of measuring the fraction of DNA molecules which are methylated at a given CpG marker. In the Illumina 450K methylation array, this fraction is referred to as Beta (or $\beta$) value which range from 0 (fully unmethylated) to 1 (fully methylated). Alternatively, the Beta (or $\beta$) score can range from $-0.5$ (fully unmethylated) to 0 (50% methylated) to 0.5 (fully methylated), after 0.5 is subtracted from the original scale (as employed by the UCSC cancer Genomics Browser). Using this scale, a sample is considered to contain a low level of methylation at cg17197774, and thus the tumor sample is deemed to be a high risk sample, if the $\beta$ score is in the range of from $-0.5$ to $-0.25$; a sample is considered to contain a high level of methylation at cg17197774, and thus the tumor sample is deemed to be a low risk sample, if the $\beta$ score is in the range of from $+0.5$ to $+0.25$. Samples with $\beta$ score in between ($>-0.25$ but $<+0.25$) contain an intermediate level of methylation. Those of skill in the art will recognize that similar scales based on different relative numeric ranges may be developed, e.g. a scale may range from 1-10, or from $-1000$ to $+1000$, or from 0.001 to 1.000, etc. However, the conclusions that are drawn are the same, with the scale providing the ability to assign a methylation level of cg17197774 as high or low (or intermediate) for a given tumor sample.

In some aspects, the assays of the invention include an analysis of other cancer markers as well, together with measuring methylation of cg17197774. For example, the copy number of one or more genes (e.g. mda-9/Syntenin) may be determined (e.g. see issued U.S. Pat. No. 9,323,888, the complete contents of which is herein incorporated by reference, for suitable methodology); and/or the status (methylation status, copy number, etc.) of other cancer markers may be assessed, e.g. those listed in US patent applications 20160108476 and 20160102367 and issued U.S. Pat. No. 9,328,379, the complete contents of each of which is herein incorporated by reference. These references also provide methods of measuring DNA methylation, as does issued U.S. Pat. No. 9,328,343, the complete contents of which is also herein incorporated by reference.

In some aspects, MDA-9/Syntenin protein expression is also monitored, at one or the other or both of the mRNA and protein levels. Methods of measuring mRNA expression are known to those of skill in the art, e.g. RT-qPCR (reverse transcription followed by quantitative PCR), the use of a hybridization technique, e.g. with a microarray of complementary nucleic acid, etc. This can be preformed using cells from a liquid biopsy sample. The detection of protein expression is typically performed on a biopsy sample from a solid tumor via immunohistochemistry and includes the analysis of an immunostained sample (e.g. using antibodies specific for the protein to stain the protein), the analysis being done by an experienced pathologist who can measure the intensity of staining either visually or through using image analysis software. Generally, the level of protein expression in the tumor sample is compared to the level in one or more healthy tissue samples. If the level of expression in the tumor sample is higher than that of the healthy tissue (e.g. a non-cancerous control sample), then the tumor sample is positive for increased protein expression, and this is indicative of a less favorable prognosis (e.g. a poor prognosis).

mda-9/Syntenin gene copy number may also be measured, e.g. by direct sequencing of a sample, e.g. using the Fluorescence in situ hybridization (FISH) approach, by in situ hybridization or using any other standard molecular diagnostic approach. In general, if the copy number of mda-9/Syntenin in a sample is greater than that in normal tissue and/or in control samples (e.g. from non-cancerous tissue), then this may indicate a less favorable prognosis (e.g. a poor prognosis) for the patient.

In some aspects, the level of expression of downstream marker genes activated by MDA-9/Syntenin (indicators of lower promoter methylation) are determined to measure MDA-9/Syntenin indirectly. If the level of expression of one or more of such downstratem marker genes is elevated compared to that of normal tissue and/or control samples, then this is consistent with a higher risk of a poor prognosis. Exemplary genes of this category include but are not limited to insulin Growth Factor Binding Protein-2 (IGFBP-2), disintegrin and metalloproteinase with thrombospondin, amyloid, precursor protein 770, HSP90 co-chaperone CDC37, growth-regulated alpha protein (CXCL1), cysteine-rich 61/connective tissue growth factor/nephroblastoma 1 (CCN1), connective tissue growth factor 2 (CCN2), macrophage migration inhibitory factor, urokinase-type plasminogen activator, isoform 12 of CD44 antigen, agrin, long isoform of laminin subunit gamma-2, and isoform 1 of connective tissue growth factor, as described in US patent application 20130338033, the complete contents of which are hereby incorporated by reference. In some aspects, the proteins that are measured are IGFBP-2 and urokinase-type plasminogen activator (uPA). If the downstream proteins are secretory, detection may be performed by simple ELISA of samples including blood, plasma, tumor lysates, etc. Additionally—all of these proteins can also be detected by direct staining as described for MDA-9/systenin protein, or by sequencing or by quantitative PCR (qPCR). e.g. by measuring mRNA levels in cells from a liquid biopsy. This can be done via sequencing, and/or by measuring protein levels per se (e.g. by ELISA). If the level of expression of one or more marker genes is elevated compared to a suitable control, (e.g. a healthy tissue sample), this indicates a less favorable prognosis (e.g. a poor prognosis).

In some aspects, a complete "methylation signature", comprising at least one, or in some aspects at least two or more, of: the level of methylation at cg17197774, the level of expression of downstream marker genes activated by MDA-9/Syntenin, the level of expression of MDA-9/Syntenin protein and mda-9/Syntenin gene copy number, provides a complete picture and approach for diagnosing cancer, stratifying cancer patients, defining therapeutic responses in order to decide which treatment protocols to pursue, monitoring dormancy of tumors, monitoring tumor progression, monitoring tumor activation, etc. For example, if the level of methylation at cg17197774 is low and the level of one or more of mda-9/Syntenin gene copy number, the level of expression of downstream marker genes activated by MDA-9/Syntenin and the level of MDA-9/Syntenin protein is high, then a less favorable prognosis (e.g. a poor prognosis) is indicated.

Methods of Prognosis

Calculated β values are used, for example, in the prognosis of cancer. By "prognosing" we mean predicting or forecasting the likely course or outcome of a disease or ailment. As intended herein, the expression "prognosis of progression of a cancer" encompasses the prognosis, in a patient wherein the occurrence of a cancer has already been diagnosed, of various events, including: the chances of occurrence of metastasis; the chances of recurrence of cancer after treatment; and/or the chances of a long disease-free (DFS) and/or long overall survival (OS) times. For example, a good prognosis might indicate: a low likelihood of metastasis, a low likelihood of a recurrence of the cancer, either locally or at a distant site, a DFS time or an OS time of 5 years or more, etc. Conversely, a poor prognosis might indicate: a high likelihood of metastasis, a high likelihood of a recurrence of the cancer, either locally or at a distant site, a DFS time or an OS time of less than 5 years, etc. An intermediate prognosis may indicate chances that fall between these extremes. In addition, during monitoring of a cancer, a decrease in methylation may indicate that the subject has a "rising" or increasing risk of a poor prognosis. The "grade" of a tumor may be established by the present methods, with a low level of methylation indicating a high grade, highly invasive tumor and a high level of methylation indicating a low grade tumor that is unlikely to metastasize, e.g. for glioma and other cancers including but not limited to melanoma, breast, and prostate The invention provides methods involving the prognosis of cancer in a subject (patient) in need thereof. In some aspects, the patient suffers from a cancer selected from the group consisting of adrenal cortical cancer, anal cancer, bile duct cancer (e.g. peripheral cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). Generally, the cancer is characterized by the presence of at least one solid tumor.

Methods of Treatment

An exemplary use of the information provided by the methods disclosed herein is to select a suitable treatment for a patient with cancer. In general, a patient whose tumor cells have a low level of methylation at cg17197774 is categorized as having a poor prognosis and is likely in need of immediate, aggressive treatment, as well as extensive follow-up, while for an individual categorized as having a good prognosis a more limited, moderate treatment regimen is likely to suffice. Exemplary cancer treatments that are used to treat the cancer include but are not limited to: surgery (e.g. resection or "debulking" surgery); radiotherapy, chemotherapy, etc., and combinations of these. Performing the cancer prognosis method of the invention may also indicate, with more precision than the prior art methods, those patients at high-risk of tumour recurrence who may benefit from adjuvant therapy, including immunotherapy.

It is possible that a patient whose biopsy samples exhibit cg17197774 β values below 0.5 (using the 0 to 1 scale), may need to be treated more aggressively post-resection. One possible regimen is the EORTC/NCIC GBM regimen reported back in 2005 (Stupp et al, NEJM). The regimen consists of concomitant radiation (at 2 Gy given 5 days a week for 6 weeks) and temozolomide (daily at 75 mg per square meter of body-surface area per day) treatment, followed by 6 months of adjuvant temozolomide therapy (150 to 200 mg per square meter for 5 days during each 28-day cycle). On the other hand, glioma patients whose biopsy samples exhibit cg17197774 β values at least 0.5 (using the 0 to 1 scale), may require treatment considerably less aggressive than the one described above.

Glioma

In some aspects, the subject suffers from glioma. By "glioma" we mean a type of tumor that starts in the brain or spine and arises from glial cells. Gliomas are named according to the specific type of cell with which they share histological features, but not necessarily from which they originate. The main types of gliomas are: ependymomas; astrocytomas such as glioblastoma multiforme; oligodendrogliomas; brainstem gliomas; optic nerve gliomas; and mixed gliomas such as oligoastrocytomas, which contain cells from different types of glia. Each of these types of glioma is prognosed, treated, etc. by the methods described herein, and/or the methods of the invention may be used to confirm a previous diagnosis of low- vs high-grade tumor.

If the subject is, according to the methods described herein, deemed to have a good prognosis, e.g. the tumor is a low-grade, "slow growing" tumor, no treatment may be necessary. Rather, the rate of tumor growth is monitored (e.g. by MRI scanning), so-called "watchful waiting", and, depending on what is observed, no action may be taken, or treatment may ensue at a later time. Alternatively, if the tumor is a rapidly growing, high-grade tumor, immediate treatment is typically undertaken. Exemplary treatments include surgery (e.g. resection or "debulking" surgery); radiotherapy, chemotherapy, immunotherapy, etc., and combinations of these.

In the case of glioma, types of chemotherapy that may be used include but are not limited to: carmustine implants (Gliadel), temozolomide chemotherapy, combination chemotherapy such as PCV, which contains the drugs procarbazine, lomustine (CCNU) and vincristine. The methods of the invention advantageously aid in making treatment decisions. For example, if a measurement of the level of methylation at site cg17197774 indicates a high level of methylation (and hence low expression of mda-9, then a medical professional such as a physician may decide that surgery is not necessary. If debulking surgery is deemed to be warranted, and if the methylation level at site cg17197774 is high, then no further treatment may be recommended. Alternatively, if the methylation level is low, then, depending on the level (e.g. intermediate), a relatively moderate approach of radiotherapy may be recommended. However, if the level of methylation is very low, more aggressive therapy may be selected (e.g. chemotherapy before and/or during a course of radiation). In addition, if the level of methylation does not increase during a particular treatment regimen, this information is used to inform the physician that the type, amount or duration of chemotherapy should be changed (e.g. a different drug or drugs may be used, or the does might be increased, or the frequency and/or duration of the course of chemotherapy might be increased); and/or the amount and/or duration of radiation treatment should be changed (e.g. to a higher and/or more frequent dose, a longer course, etc.).

Monitoring Methylation Status

The methods described herein are also used e.g. for defining therapeutic responses and/or monitoring the methylation status of a subject on an ongoing basis. For example, methylation is measured in patients that have received a cancer treatment (e.g. chemotherapy, radiation, gene therapy, immunotherapy, etc.) that reduces the spread of metastatic cells, in order to define the post-treatment methylation status of circulating cells isolated, e.g. from different stages of disease, during and after therapy, etc. Based on the level of cg17197774 methylation that is detected, a skilled medical practitioner evaluates the results and decides what course of treatment, if any, should be undertaken.

In some aspects, the methylation status of cg17197774 is monitored throughout a patient's lifetime, or throughout the lifetime of a subject who has a known risk of developing cancer or cancer metastasis, or for a subject who does not have or is not aware of having any risk factors for cancer, etc. to determine if latent cancer is present and/or has become activated.

Kits

Kits comprising e.g. oligonucleotide primers and/or antibodies suitable for carrying out the measurements described herein are also encompassed by the invention.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Examination of Epigenetic and Other Molecular Factors Associated with mda-9/Syntenin Dysregulation in Cancer Through Integrated Analyses of Public Genomic Datasets Abstract mda-9/Syntenin (Melanoma differentiation-associated gene 9), also known as SDCBP, encodes a double PDZ-domain containing protein involved in multiple cellular functions. Recent studies indicate that mda-9 plays important roles in cancer progression and invasion. This Example describes genetic and epigenetic factors which elevate mda-9 expression levels as cancer progresses and the molecular pathways and functionalities associated with mda-9's dysregulation. Publicly available genomic databases were used for these analyses, the majority of which were genome-wide expression, copy number, and methylation datasets for various cancer types generated by The Cancer Genome Atlas (TCGA). Also included were a number of expression datasets available from NCBI's Gene Expression Omnibus (GEO), as well as information taken from the ENCODE Project, and the Human Protein Atlas. Seminal observations were made including the following: a) mda-9 expression correlates with both copy number and the methylation status of a key intronic CpG site (cg17197774) located downstream of the CpG island, b) Like mda-9 expression, methylation at cg17197774 is a prognostic marker in glioma, c) Of the cancer types analyzed, melanoma exhibits the highest level of mda-9 expression and a generally hypomethylated cg17197774 CpG site, Background on mda-9/Syntenin mda-9/Syntenin (Melanoma differentiation-associated gene 9), also known as SDCBP (Syndecan binding protein), is a human gene transcribed in the plus strand of 8q12.1 region. The gene consists of 9 exons (including the UTR regions), and has 5 transcript variants coding for 3 protein isoforms. Isoforms 1, 2 and 3, code for proteins with 298, 292 and 297 amino acids respectively. As indicated in the UCSC genome Browser (genome.ucsc.edu), there is a possible $10^{th}$ exon 3' of the 5' UTR exon, which may result in an even longer isoform (318 aa). The prominent features of the protein (isoform 1 is 33 KDa) are its two PDZ domains (PDZ1 and PDZ2). PDZ domains, due to their repertoire of possible interactions (C-terminal peptide recognition, interactions with internal peptide ligands, PDZ-PDZ interactions, PDZ-phospholipid interactions), are known to mediate a wide array of signaling pathways and cellular functions. Among the molecules the protein interacts with are, phosphoinositides, IL-5 receptor α (IL5RA), proTGFα, syndecan, eIF5A, Schwannomin and CD6. A short list of cellular processes involving MDA-9 are: axon outgrowth, chemotaxis HIV-entry. development of neuronal membrane architecture protein cell surface localization, cell adhesion and pro-metastatic and pro-angiogenic activities.

mda-9 plays an important role in cancer progression, particularly during the invasion/metastasis stage. Studies have demonstrated that MDA-9 is a positive regulator of metastasis in melanoma partially attributed to its interaction with c-Src, which eventually leads to the activation of the transcription factor NF-κB These changes induce an increase in the transcription of matrix metalloproteinases (MMPs), necessary for the degradation of extracellular matrix during invasion. MDA-9's interaction with c-Src may also lead to transcriptional activation of insulin growth factor binding protein 2 (IGFBP2), which can promote angiogenesis in melanoma. mda-9 is also over-expressed in metastatic as well as ER-negative breast cancer. mda-9's regulation of cell migration was also demonstrated in colorectal cancer. a cancer type in which poor clinical outcome is associated with elevated expression of this gene. Another recent finding is mda-9's regulation of urothelial cell proliferation through its modulation of EGFR signaling.

Despite the wealth of mda-9-related knowledge listed above, there is still much to learn regarding mda-9 and its involvement in cancer progression. One area that has not previously been investigated is how genetic and epigenetic factors contribute to its elevated expression during cancer progression. For any gene, two factors that can lead to elevated expression are: a gain or amplification of copy number, and reduced methylation at the appropriate CpG site on its promoter region. However, these are by no means the only factors that influence the transcription of a gene. The activation of transcription factors and upstream signaling pathways are also necessary for a gene's transcriptional activation. The activities of DNA methyltransferases (DNMTs), which initially methylate the CpG sites, may also factor in a gene's dysregulation.

The availability of comprehensive and publicly available genomic datasets (such as genome-wide expression, methylation and copy number data) for various types of cancer permitted us to carry out an in-silico analysis of the genetic and epigenetic factors associated with mda-9's transformation into a cancer- or metastasis-promoting state, as described herein.

Publicly Available Cancer Genomic Datasets

In the past decade, cancer-related data generated using various genome-wide molecular profiling tools have been made publicly available. Two very extensive repositories are NCBI's Gene Expression Omnibus (GEO) (www.ncbi.nlm.nih.gov/geo/) and EMBL's Array Express (www.ebi.ac.uk/arrayexpress/). A huge proportion of these datasets are genome-wide expression profiles (as well as genome-wide methylation and copy number data) of cancer tissue samples, cell lines and mouse models. The most comprehensive and organized cancer genomic repository is The Cancer Genome Atlas (TCGA) (tcga-data.nci.nih.gov/tcga/). (Kaiser, 2005), TCGA has now examined the genome-wide expression (mRNA, miRNA, exon, limited protein), copy number variations, methylation status and mutations in more than 20 adult cancer types (a total of more than 6000 tissue samples). The primary advantages of TCGA datasets are: a) each patient sample is accompanied by very comprehensive clinico-pathological data (e.g., follow up survival records, TNM staging, treatment records), b) a huge portion of the samples have integrated molecular profiles (i.e., same sample being profiled for expression, copy number, sequence, methylation), c) many of the tumor samples have matched normals and d) the data are generated using the latest and widely considered standards in molecular profiling technology. These include Illumina HiSeq 2000 for expression profiling, Illumina Infinium 450k BeadChip for methylation analysis, Affymetrix SNP 6 array for copy number analysis, and various Next Gen Sequencing platforms for mutational profiling. Also available to the public is the Human Protein Atlas Database (www.proteinatlas.org/) (Uhlen et al., 2010). This database is a genome-wide immunohistochemical staining analyses portal of a large number of human tissues, cancers and cell lines. Another data repository is ENCODE (Encyclopedia of DNA Elements) (genome.ucsc.edu/ENCODE/, a project which aims to build a comprehensive list of functional elements in the human genome, and further understanding of gene regulation. In ENCODE, numerous experimental tools, such as ChIP Seq technology, were employed to examine how proteins (e.g., transcription factors, histones) recognize and bind to genomic sequences such as promoter regions.

Specific Datasets Examined for mda-9 Analysis and the Analytical Approaches Employed Publicly Available Genomic Datasets.

This Example describes a rigorous examination of various public genomic datasets to investigate mda-9/Syntenin's genetic and epigenetic regulation Most datasets originated from TCGA, and some were downloaded from NCBI-GEO (Table 1). Specifically, the Illumina HiSeq 2000 (expression), Illumina Infinium 450k BeadChip (CpG Methylation), and Affymetrix SNP 6-derived GISTIC2 copy number datasets for TCGA Glioma (combined Glioblastoma Multiforme and Lower Grade Glioma; GBM and LGG, respectively), Skin Cutaneous Melanoma (SKCM), Liver Hepatocellular Cancer (LIHC), Prostate Adenocarcinoma (PRAD), Colon Adenocarcinoma (COAD) and Kidney Renal Papillary Cell Carcinoma (KIRP) were analyzed. In addition, the TCGA Pan Cancer (PANCAN) dataset was also examined. The TCGA datasets, generated and processed (as level 3 data) at TCGA Genome Characterization (and Data Coordination) Centers, were downloaded in normalized matrix format from the UCSC Cancer Genomics Browser (https://genome-cancer.ucsc.edu/) (Zhu et al., 2009; Goldman et al., 2013). All of the relevant clinical information was downloaded along with the genomic data. Also analyzed were tissue expression datasets from GEO: GSE4290 (glioma) (Sun et al., 2006), GSE3189 (melanoma) (Talantov et al., 2005) and GDS2545 dataset (prostate cancer) (Chandran et al., 2007). These datasets were generated using Affymetrix HG U133 Plus 2, U133A, and U95A arrays, respectively. The MDA-9 protein expression levels were also assessed in the Human Protein Atlas Database (www.proteinatlas.org/). Immuno-histochemical images and other data were downloaded directly from the website. CpG methylation data (Ilumina 450k) for cell lines included in the ENCODE project, generated from Hudson Alpha Inst. (R. M. Myers lab; Hunstsville, Ala.) were downloaded from the UCSC Genome Browser. Other information from the ENCODE project, such as the ChIP Seq-derived quantification of DNA-bound modified histones (B.E. Bernstein lab, Broad Inst., Cambridge, Mass.) were viewed and images captured through the UCSC Genome Browser.

TABLE 1

The list of publicly available genomic datasets analyzed for the study

| Dataset ID | Cancer Type | Platform | No. Cancer | No. Normal |
|---|---|---|---|---|
| A. Genome-wide Expression | | | | |
| TCGA_GBM[a] | Glioma (Glioblastoma Multiforme) | Illumina Hi Seq 2000 | 168 | 0 |
| TCGA_LGG | Glioma (Lower Grade Glioma) | Illumina Hi Seq 2000 | 205 | 0 |
| TCGA_LIHC | Liver Hepatocellular Carcinoma | Illumina Hi Seq 2000 | 69 | 36 |
| TCGA_PRAD | Prostate Adenocarcinoma | Illumina Hi Seq 2000 | 142 | 37 |
| TCGA_KIRP | Kidney Renal Papillary Cell Carcinoma | Illumina Hi Seq 2000 | 76 | 25 |
| TCGA_PANCAN[b] | Pan Cancer (Combination of 22 Cancer Types) | Illumina Hi Seq 2000 | 5453 | 587 |
| GSE4290b[c] | Glioma (all grades) | Affymetrix HG U133 Plus 2 Array | 153 | 23 |
| GSE3189[c] | Melanoma | Affymetrix HG U133A Array | 45 | 7 |
| GDS2545[c,d] | Prostate Cancer | Affymetrix HG U95A Array | 90 | 81 |
| B. Genome-wide copy number | | | | |
| TCGA_GBM | Glioma (Glioblastoma Multiforme) | Affymetrix SNP 6 Array | 544 | N/A |
| TCGA_LGG | Glioma (Lower Grade Glioma) | Affymetrix SNP 6 Array | 206 | N/A |
| TCGA_LIHC | Liver Hepatocellular Carcinoma | Affymetrix SNP 6 Array | 97 | N/A |
| TCGA_COAD | Colon Adenocarcinoma | Affymetrix SNP 6 Array | 413 | N/A |
| TCGA_PRAD | Prostate Adenocarcinoma | Affymetrix SNP 6 Array | 187 | N/A |
| TCGA_KIRP | Kidney Renal Papillary Cell Carcinoma | Affymetrix SNP 6 Array | 127 | N/A |
| TCGA_SKCM | Skin Cutaneous Melanoma | Affymetrix SNP 6 Array | 260 | N/A |
| C. Genome-wide CpG methylation | | | | |
| TCGA_GBM | Glioma (Glioblastoma Multiforme) | Illumina Methylation 450K Beadchip Array | 121 | 0 |
| TCGA_LGG | Glioma (Lower Grade Glioma) | Illumina Methylation 450K Beadchip Array | 204 | 0 |
| TCGA_LIHC | Liver Hepatocellular Carcinoma | Illumina Methylation 450K Beadchip Array | 98 | 50 |
| TCGA_COAD | Colon Adenocarcinoma | Illumina Methylation 450K Beadchip Array | 258 | 38 |
| TCGA_PRAD | Prostate Adenocarcinoma | Illumina Methylation 450K Beadchip Array | 192 | 49 |
| TCGA_KIRP | Kidney Renal Papillary Cell Carcinoma | Illumina Methylation 450K Beadchip Array | 111 | 45 |

TABLE 1-continued

The list of publicly available genomic datasets analyzed for the study

| Dataset ID | Cancer Type | Platform | No. Cancer | No. Normal |
|---|---|---|---|---|
| TCGA_SKCM | Skin Cutaneous Melanoma | Illumina Methylation 450K Beadchip Array | 338[d] | 1 |

Notes:
[a]All of TCGA datasets and accompanying clinico-pathological information were downloaded as pre-processed data, through the UCSC Cancer Genomics Browser (https://genome-cancer.ucsc.edu).
[b]The TCGA Pan Cancer (PANCAN) dataset is mean-normalized, consisting of 22 TCGA datasets. Normals were not analyzed for this study.
[c]These datasets were downloaded from the NCBI Gene Expression Omnibus (GEO) site (ncbi.nlm.nih.gov/geo/)
[d]Tumor samples include 267 metastatic and 71 primary tumors.

Analytical Tools.

A number of genomic and statistical tools were employed for this study. Initial manipulations of the downloaded datasets were done using Gene-E (Broad Institute, Cambridge, Mass.). Statistical analyses were performed using JMP Pro 10 software (SAS, Cary, N.C.), Gene-E and Gene Set Enrichment Analysis (Subramanian et al., 2005) (GSEA; Broad Inst., Cambridge, Mass.). Crucial to the analyses was information gathered from the UCSC Genome Browser, UCSC Cancer Genomics Browser, Human Protein Atlas, MsigDB (website at broadinstitute.org/msigdb) (Liberzon et al., 2011), Reactome (reactome.org) (Joshi-Tope et al., 2005), KEGG pathway database (website at genome.jp/kegg/) and Biocarta (www.biocarta.com). Accessed through the UCSC Genome Browser were results from ENCODE Chromatin State Segmentation using Hidden Markov Modeling (Ernst and Kellis, 2010; Ernst et al., 2011). Necessary gene and probeset annotations were downloaded from HGNC (www.genenames.org/) and NCBI-GEO.

Patterns of mda-9 Expression During Cancer Progression and their Clinical Implications in Different Cancer Types Glioma.

Figure 1B:
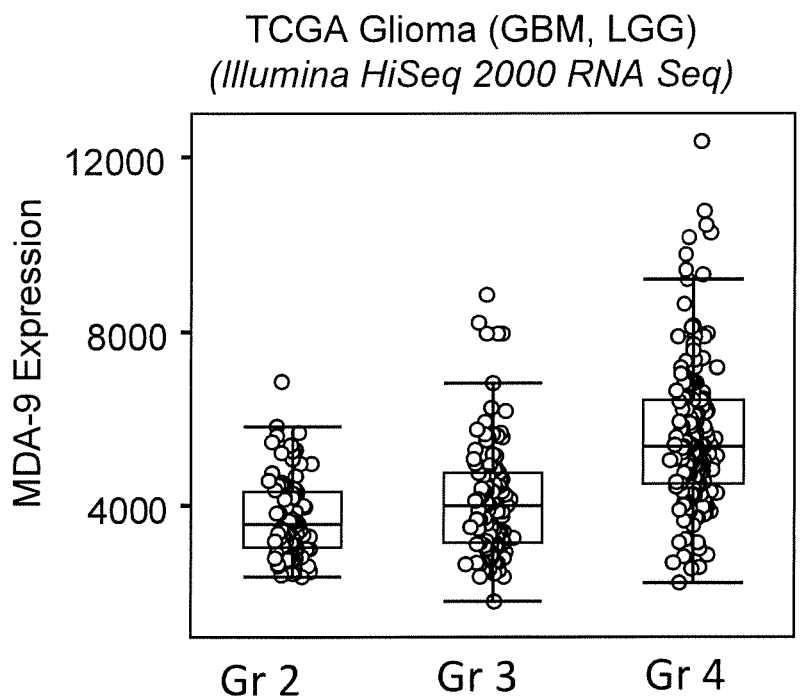
Figures 1C, 1D:
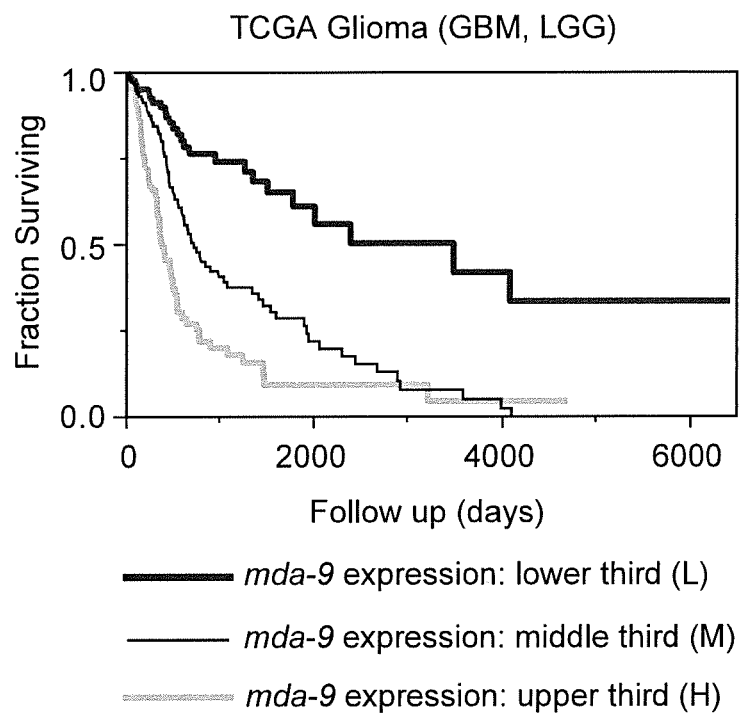
Figure 2A:
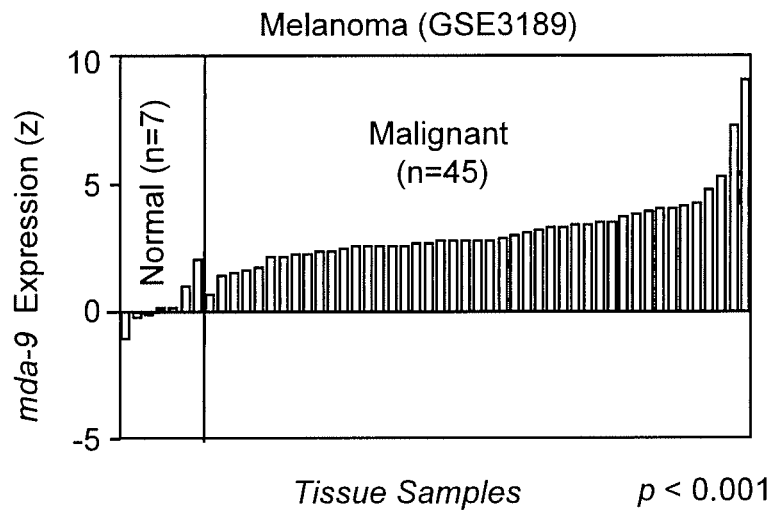
FIG. 2A-D. The expression of mda-9 (relative to normal samples) in melanoma (A), prostate (B), liver (C) and kidney renal papillary cell cancer. The expression values were derived from public genome-wide expression datasets. The relative expression (z) is calculated as $z=(I_n-\text{Ave. } I_{norm})/sd_{norm}$, where n refers to every sample (including tumors), while norm refers to normal samples only. Inset are the resulting p values for t-test comparing the normal and tumor sample groups.
Figure 2B:
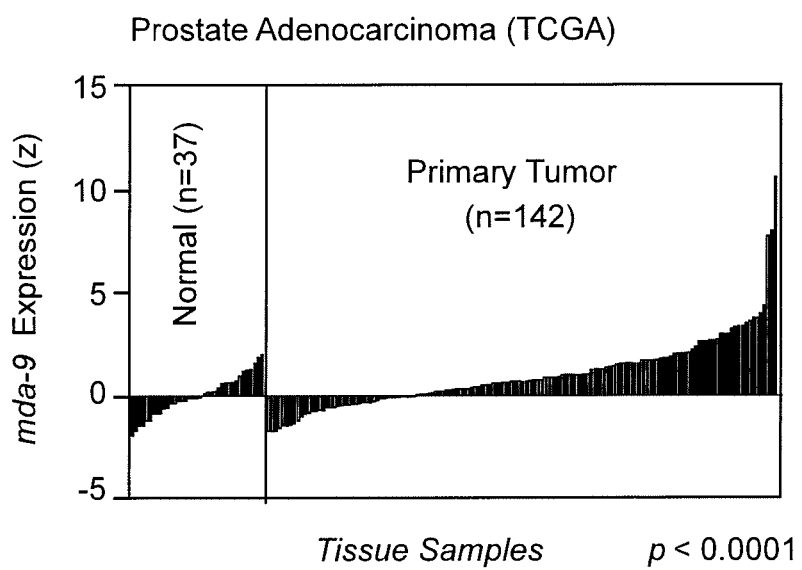
Figure 2C:
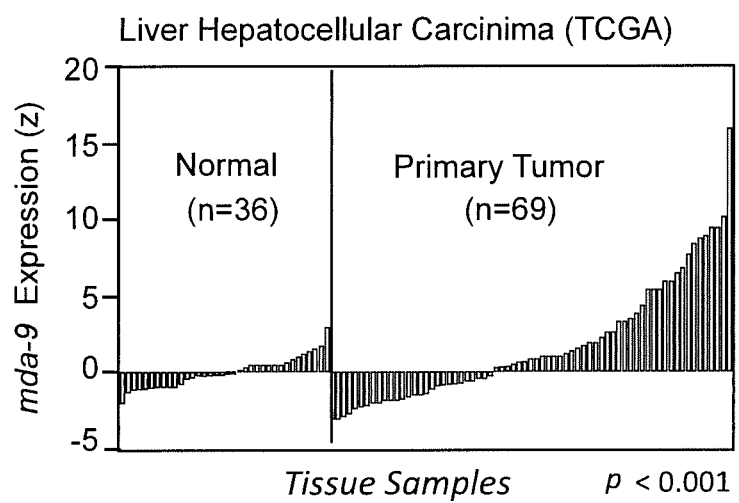
Figure 2D:
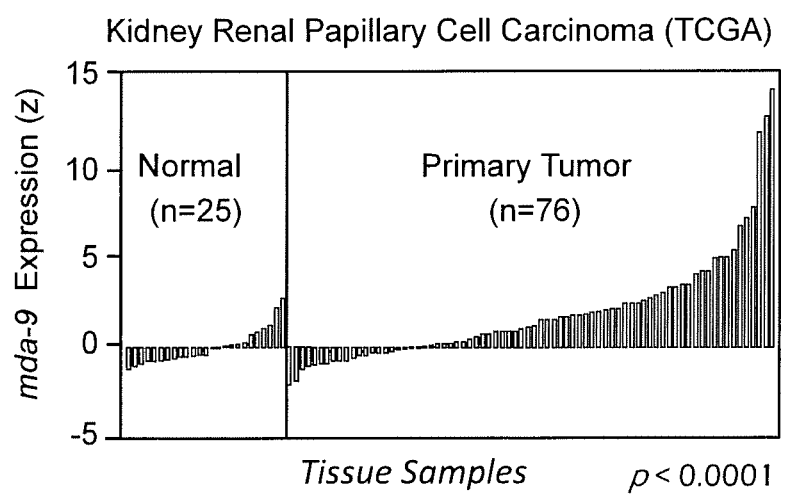

The first dataset examined was GSE4290 (rembrandt-db.nci.nih.gov) (Sun, et al., 2006), generated using the Affymetrix platform HG U133 Plus 2. As shown in FIG. 1A, mda-9 expression levels increase as one progresses from lower towards higher tumor grades, as compared to normal tissues (ANOVA, $p<0.001$). The same trend can be seen upon analysis of the combined TCGA GBM and LGG datasets, which were generated using an entirely different platform (i.e., Illumina Hi Seq 2000) (ANOVA, $p<0.001$) (FIG. 1B). However, unlike the GSE4290, the TCGA glioma dataset did not include normal tissue samples. In the Kaplan-Meir graph shown in FIG. 1C, the TCGA glioma samples were divided into 3 subgroups according to mda-9 expression levels: lower third (L), middle third (M), and upper third (H). Results show that the H and M subgroups had much worse overall survival rates compared to the L subgroup. Unfortunately, the GSE4290 was not annotated with follow up records, thus could not be subjected to survival analysis. FIG. 1D, the data presented in tabular form.

Melanoma, Prostate Cancer, Liver Hepatocellular Carcinoma and Kidney Renal Papillary Carcinoma.

The upregulation (relative to normals) of mda-9 is also evident in other tumor types, as shown in FIG. 2A-D. The distribution of mda-9 expression levels in tumor and normal tissue groups for the four cancer types are shown in order of increasing z score (relative expression), calculated as $(I_n - \text{Average } I_{norm})/\text{standard dev}_{norm}$, where n refers to every sample (including tumors), while norm refers to normal samples only. Student t-test indicate that mda-9 expression levels in tumors are significantly higher compared to normals. The mda-9 levels for prostate cancer, liver hepatocellular carcinoma and kidney renal papillary carcinoma were all extracted from the TCGA RNA Seq datasets. The TCGA dataset for melanoma (SKCM) was not used for this particular part of the analysis, because the dataset did not include normal samples. Most of the TCGA SKCM samples were classified as metastasis (which is discussed as a component of the TCGA Pan Cancer dataset). Instead, the dataset GSE3189 (Talantov, et al., 2005) was analyzed to differentiate the expression levels of normal skin and malignant melanoma samples. The original GSE3189 dataset includes nevi samples, which were not included in this analysis.

mda-9 Expression in Metastasis Samples.

Figure 3:
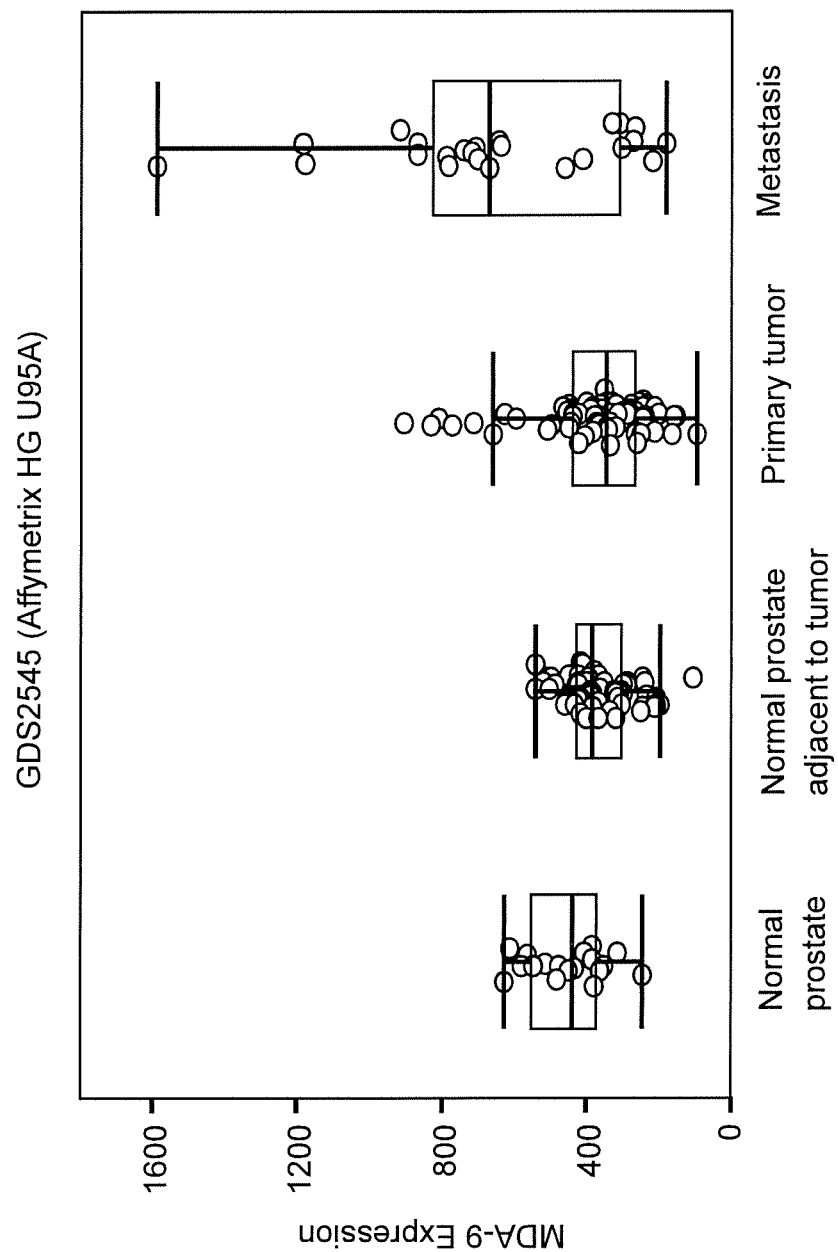
FIG. 3. Comparative mda-9 expression profiles of normal, primary tumors and metastatic prostate cancer (normal prostate; Normal prostate adjacent to tumor; primary tumor; metastasis).

The data described above were those of mda-9 transcription levels in primary tumors. Given that recent experimental results point to mda-9's role in invasion, it was of interest to examine its expression pattern in a cohort, which includes metastasis samples. Shown in FIG. 3 is data taken from the GDS2545 dataset (Chandran, et al., 2007) generated using the Affymetrix U95A array. As the graph indicates, there is a progressive increase in mda-9 levels during the progression from normal samples to primary tumor and to metastasis (ANOVA, $p<0.0001$).

mda-9 Expression Correlates with Both Gene Copy Number and the Methylation Status of cg17197774 mda-9 RNA Expression Generated Illumina HiSeq Data.

The total RNA for each TCGA tissue sample was quantitated using the Illumina HiSeq 2000 RNA Sequencing platform (performed at a TCGA Genome Characterization Center). The matrix form dataset (which is the merging of individual level 3 processed dataset) was downloaded from the UCSC Cancer Genomics Browser and the samples annotated with the accompanying clinical data. Each dataset included the expression levels for 20,501 genes. From these datasets, the transcript levels of mda-9 were derived and further analyzed.

mda-9 Copy Number as Determined by Affymetrix SNP Array.

The genome-wide copy number data for TCGA samples were also generated in TCGA Genome Characterization Centers, using Affymetrix Genome-wide Human SNP Array 6.0, consisting of probes for more than 906,600 SNPs, in addition to more than 946,000 probes for the detection of copy number variations. The experimental protocol described in the user manual can be downloaded from the company website (www.affymetrix.com). The TCGA FIRE-HOSE pipeline (Broad Institute, Cambridge, Mass.) employed the GISTIC2 algorithm (Mermel et al., 2011) to generate copy number estimates (CN) for the genes mapped in the genome. The GISTIC2 estimate for mda-9 was then extracted from the dataset, and converted to copy number, calculated using the formula: CN=2^ (GISTIC2+1)

mda-9 CpG Sites Interrogated in Illumina 450K Array.

The genome-wide CpG methylation data for TCGA samples were generated using the Illumina Infinium Human Methylation 450K platform, currently the array platform with the greatest coverage (more than 480,000 CpG sites interrogated in the entire human genome) (Sandoval et al., 2011). Bead Studio software was employed to generate beta values, which range from 0 (fully unmethylated) to 1 (fully methylated). The UCSC offset value was used in which −0.5 was subtracted from the original scale, resulting in beta values ranging from −0.5 (fully unmethylated) to 0 (50% methylated) to 0.5 (fully methylated). A total of 13 mda-9 locus CpG sites covered in the Illumina 450K array registered beta values in the TCGA datasets (see Table 2).

sites were mostly unmethylated across all the cancer datasets. This suggests that only the variation in the beta values of the two CpG sites translate to variation in mda-9 expression levels. The CpG site cg17197774 is exactly 1105 bases from the 3' edge of the CpG island while cg10129404 is part of the 3' UTR, making it less likely for the latter to be a factor in transcription of mda-9. For glioma, methylation at the CpG sites decreases as the tumor grade progresses. For liver cancer, colon adenocarcinoma and kidney papillary carcinoma, methylation at these sites decreases during the transformation from solid normals to primary tumor. There are only a few normal samples in the SKCM dataset, but it is very clear that primary and metastatic SKCM samples had the lowest levels of methylation (compared to the other 5 datasets). There was only a minimal change in methylation in primary prostate cancer relative to solid normals.

TABLE 2

List of the MDA-9 CpG sites interrogated in the Illumina Infinium 450 K Beadchip array; S Shore refers to a CpG sites located 3' from the CpG island cluster.

| Probe ID | Strand | Chr | Coordinate (build 37) | Relation to UCSC CpG Island | UCSC Ref GeneGroup | Forward Sequence | SEQ ID NO: |
|---|---|---|---|---|---|---|---|
| cg20052227 | R | 8 | 59465520 | Island | TSS1500 | GTGGGTGGCA[CG]GGGCCCGCGG | 1 |
| cg02896624 | R | 8 | 59465528 | Island | TSS1500 | GCACGGGGCC[CG]CGGGCACGAA | 2 |
| cg17984783 | F | 8 | 59465536 | Island | TSS200 | CCCGCGGGCA[CG]AACAGCCGAA | 3 |
| cg26656684 | F | 8 | 59465596 | Island | TSS200 | CAGCGGACAG[CG]GGCGGCATGA | 4 |
| cg11550426 | F | 8 | 59465608 | Island | TSS200 | CGGCATGAAC[CG]CCCCACTTTG | 5 |
| cg27280034 | F | 8 | 59465624 | Island | TSS200 | CCCACTTTGC[CG]GATACCTGGA | 6 |
| cg06294637 | F | 8 | 59465768 | Island | 1stExon; 5'UTR | GCCTCGGGGG[CG]GTCCTCGGGC | 7 |
| cg07798892 | F | 8 | 59465776 | Island | 1stExon; 5'UTR | GGTCCTCGGG[CG]CGCACCGCTC | 8 |
| cg20848390 | F | 8 | 59465780 | Island | 1stExon; 5'UTR | TCCTCGGGCG[CG]CACCGCTCTC | 9 |
| cg02103294 | R | 8 | 59465972 | Island | 5'UTR | GCATCCTGGT[CG]CAGCCGTTTT | 10 |
| cg12046629 | R | 8 | 59466300 | S_Shore | 5'UTR | TCCCAGTGCT[CG]GCGTTTCTAG | 11 |
| cg17197774 | F | 8 | 59467208 | S_Shore | 5'UTR | TAATGGTTGC[CG]GTTAAATGTA | 12 |
| cg10129404 | R | 8 | 59494304 | na | 5'UTR | TTAAAATTCA[CG]GCACCATGGA | 13 |

Figures 4A, 4B:
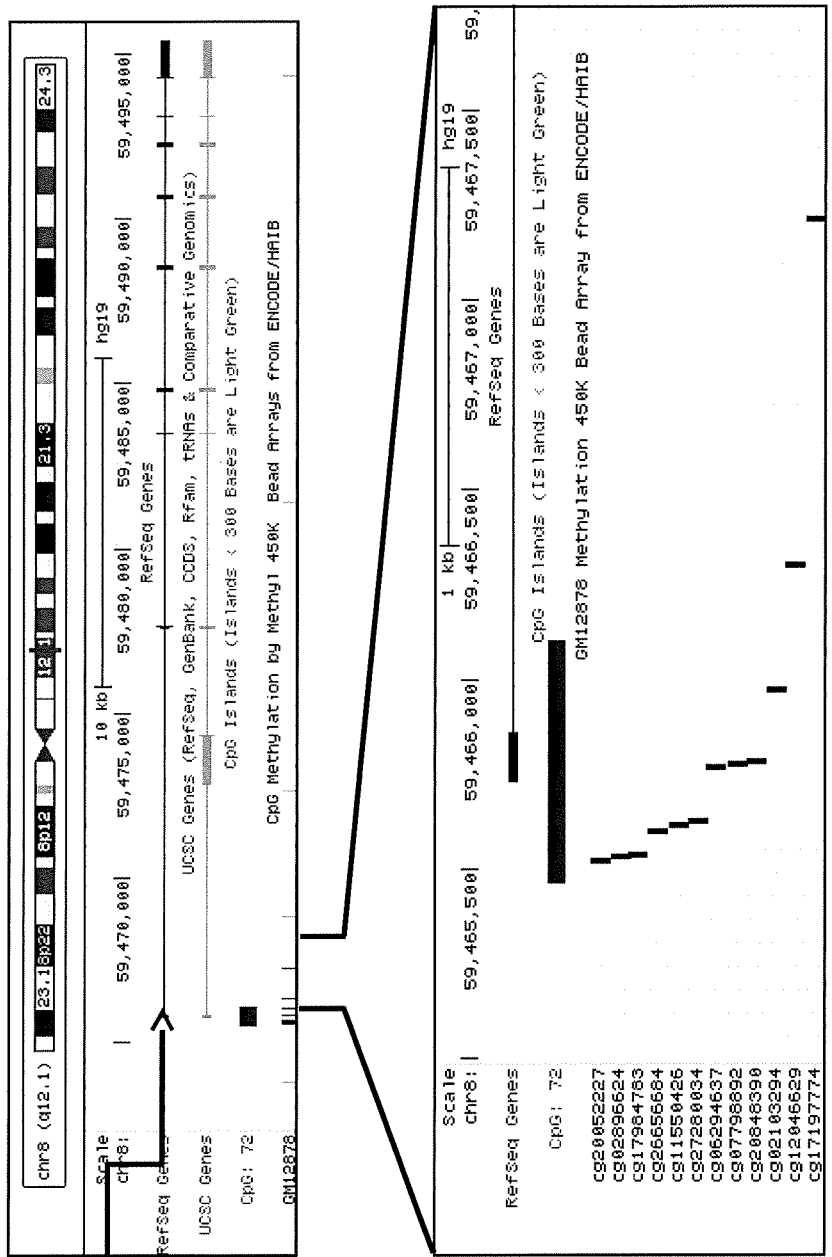
FIGS. 4A and B. A. The locus map of mda-9 with the 9 identified exons in RefSeq. UCSC Genes prediction identified a 10th exon, after the 5' UTR exon. B. Higher resolution of the promoter region, indicating the locations of the interrogated CpG sites.
Figure 5A:
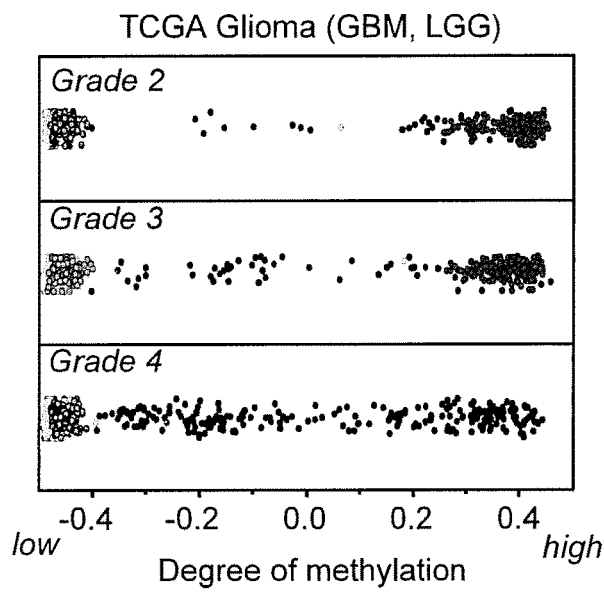
FIG. 5A-F. The degree of methylation, ranging from totally unmethylated (−0.5) to totally methylated (0.5), at the 13 CpG sites interrogated in Illumina 450K array, for tissue samples belonging to 6 TCGA cancer groups. A, glioma; B, LIHC (liver hepatocellular carcinoma); C, SKCM (skin cutaneous melanoma); D, COAD (colon adenocarcinoma); E, KIRP (kidney renal papillary cell carcinoma) and F, PRAD (rostate adenocarcinoma). Of the 13 sites, the most differentially methylated is cg17197774, followed by cg10129404.
Figure 5B:
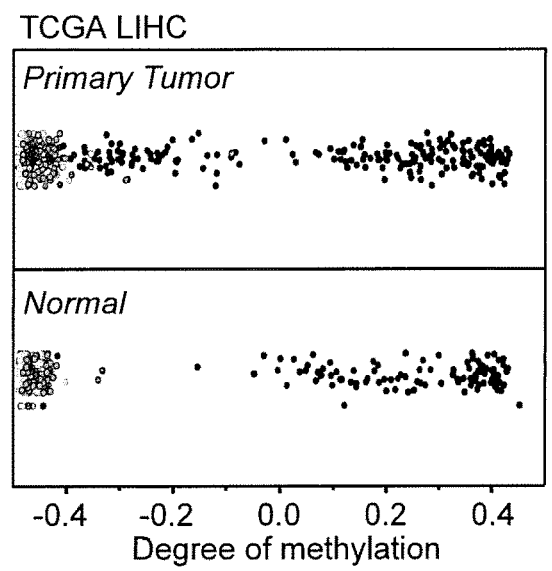
Figure 5C:
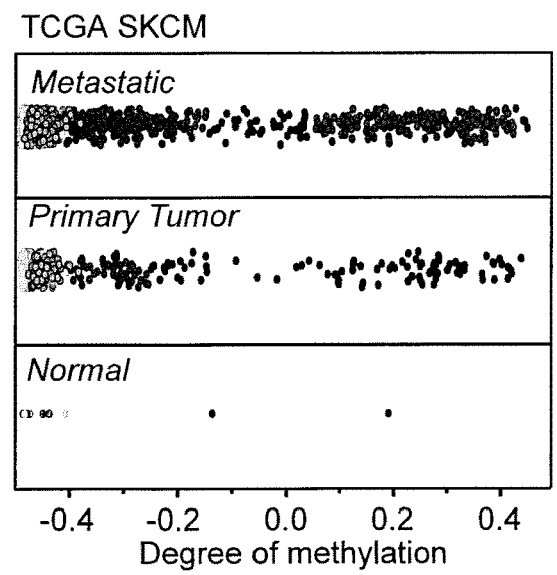
Figure 5D:
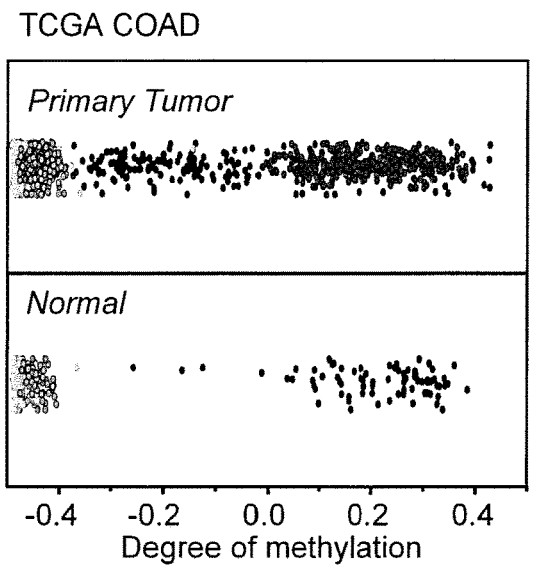
Figure 5E:
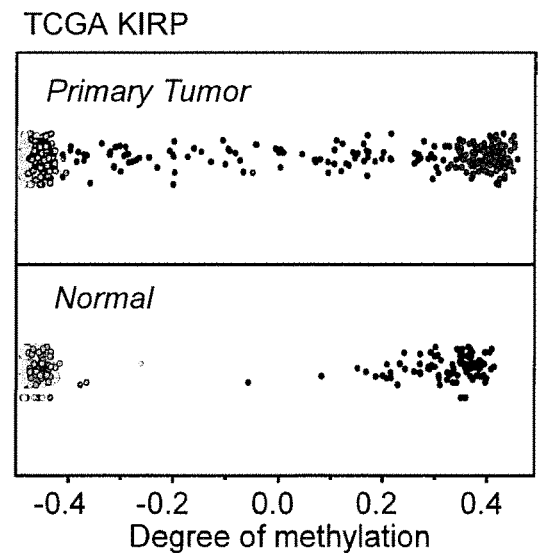
Figure 5F:
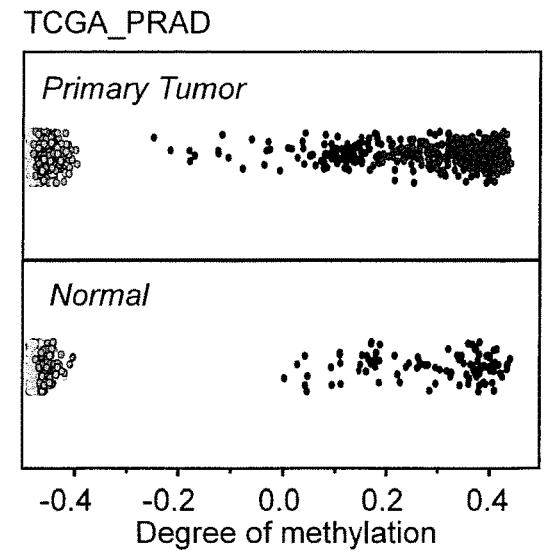
Figure 6A:
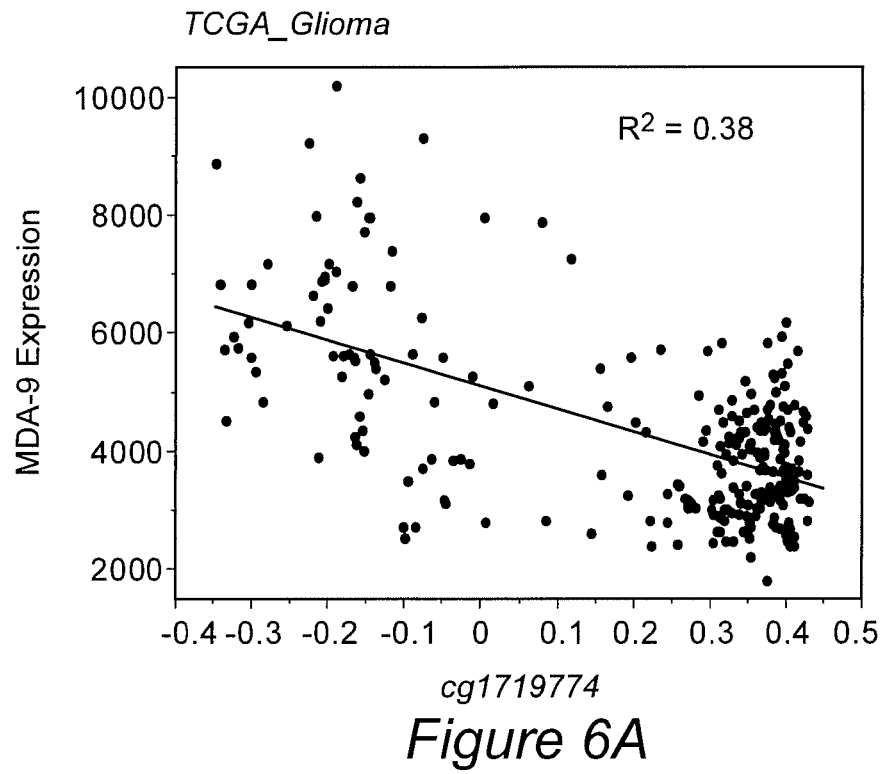
FIG. 6A-D. In both TCGA glioma and KIRP, mda-9 expression is clearly influenced by the methylation status of cg17197774 (the CpG site close to 5' UTR) and not by cg10129404 (the CpG site at 3' UTR). A, TCGA glioma cg17197774; B, TCGA glioma cg10129404; C, TCGA KIRP cg17197774; B, TCGA KIRP cg10129404.
Figure 6B:
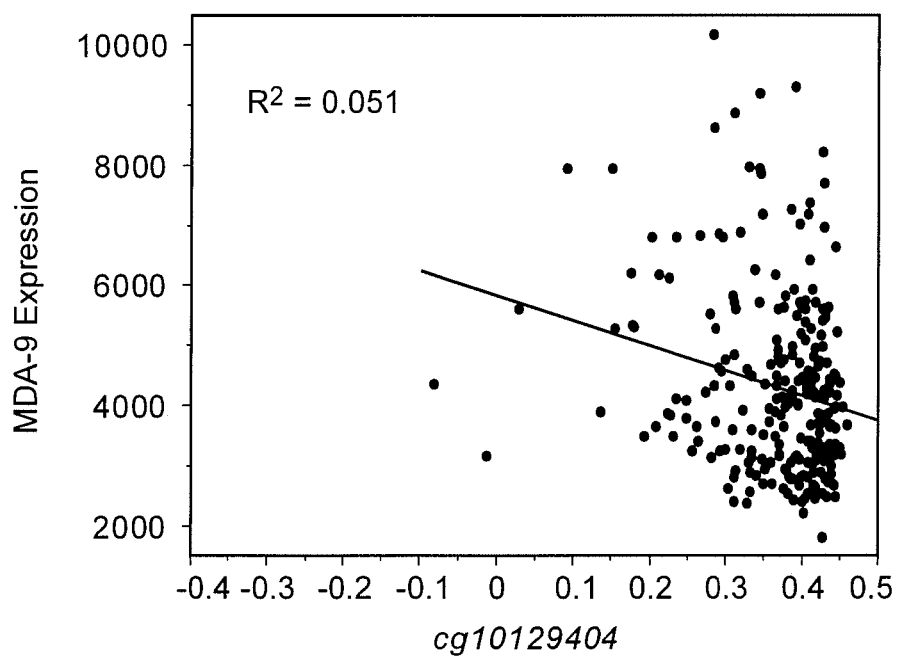
Figure 6C:
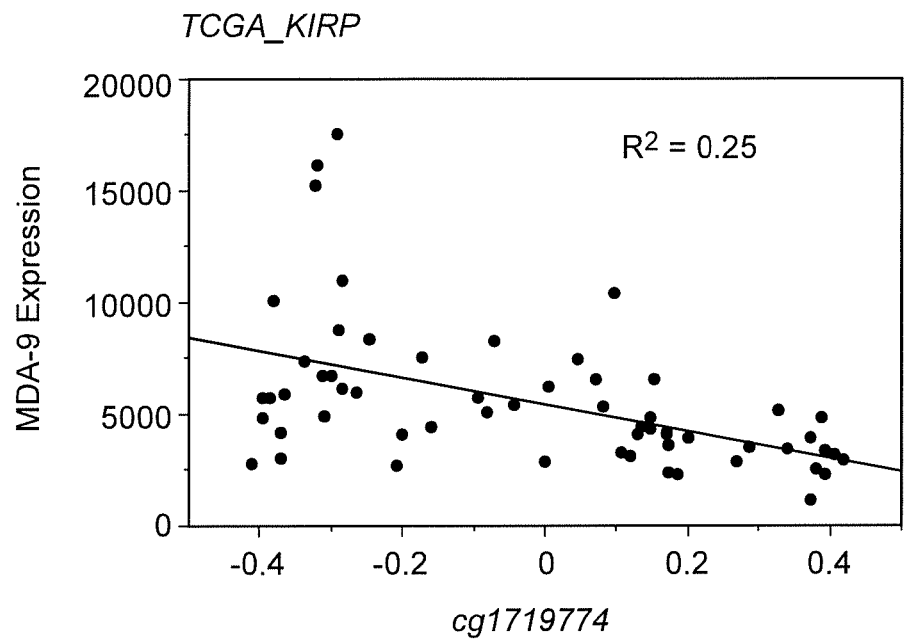
Figure 6D:
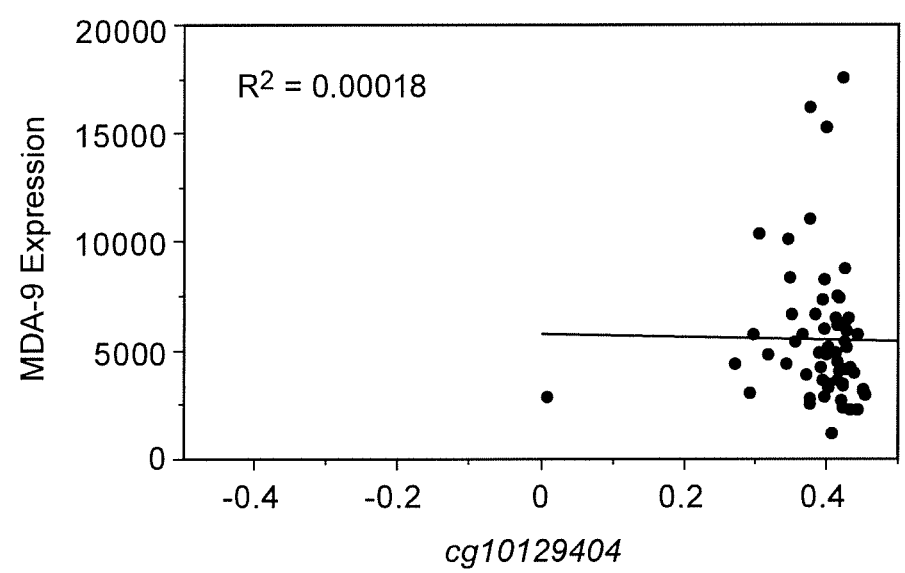
Figure 7A:
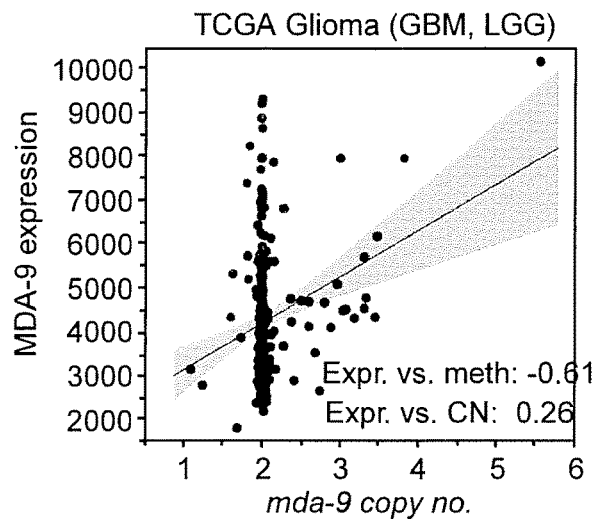
FIG. 7A-F. The expression of mda-9 as a function of its copy number and methylation at cg17197774, among six TCGA datasets. A, TCGA glioma; B, TCGA LIHC; C, TCGA SKCM; D, TCGA COAD; E, TCGA KIRP; F, TCGA PRAD.
Figure 7B:
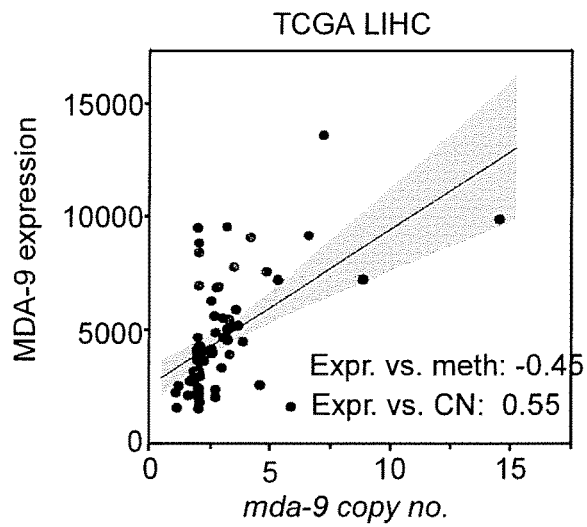
Figure 7C:
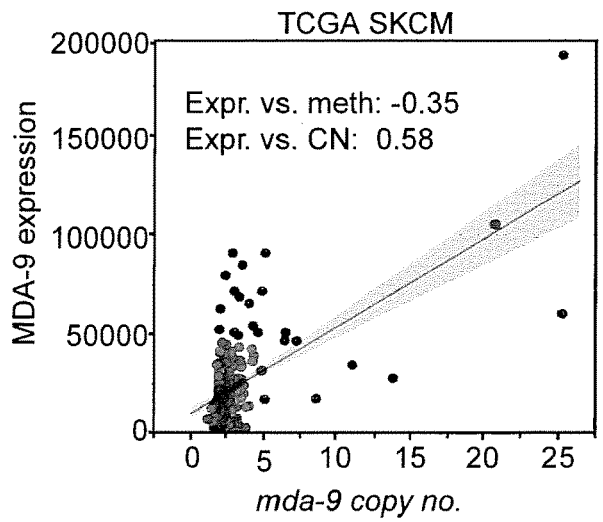
Figure 7D:
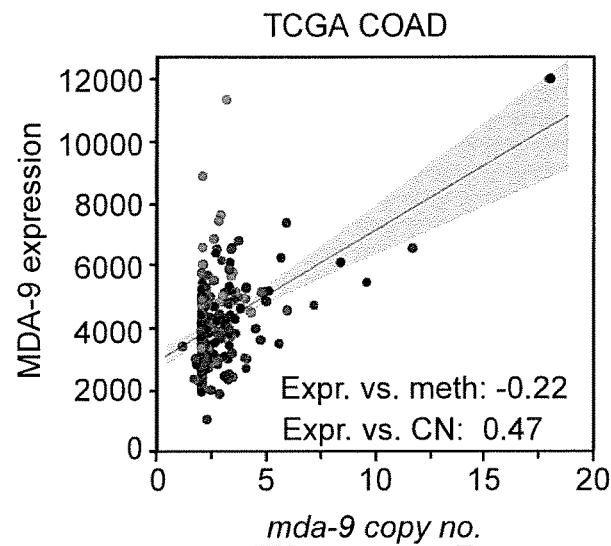
Figure 7E:
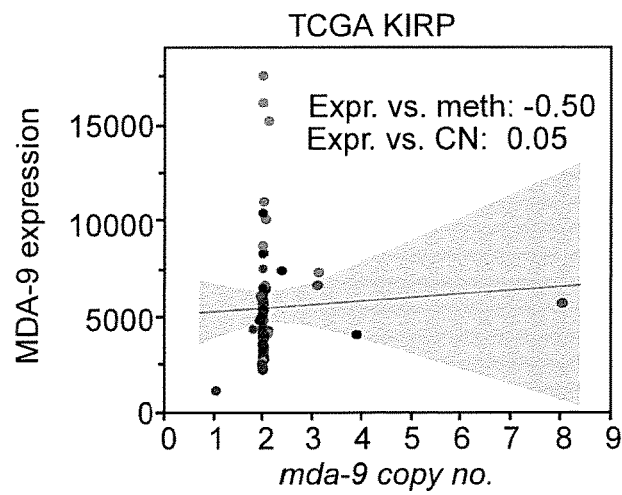
Figure 7F:
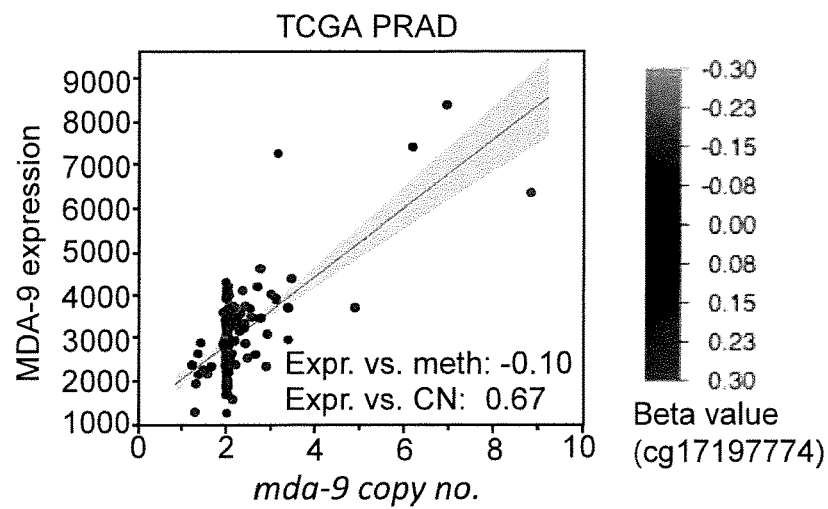

Ten of the probes are part of the CpG island group located in the promoter region, with the first five located within the transcription start sites (TSS1500, TSS200) and the next five as part of the 5' UTR exon (see FIGS. 4A and B). The next 5 CpG sites are located in the intervening introns and the last one within the 3' UTR exon. The distributions of the beta values, corresponding to each of the 13 CpG sites for each of the 6 TCGA cancer datasets, are shown in FIG. 5A-F. Except for two (cg17197774 and cg10129404), the CpG Which Amongst the Two CpG Sites Influence mda-9 Expression?

As mentioned above, it is unlikely that the 3' UTR CpG site cg10129404 influences mda-9 transcript levels. A simple analysis was conducted by plotting mda-9 expression vs the beta value for cg17197774 and cg10129404 for two select TCGA datasets (glioma and KIRP, Kidney Renal Papillary Cell Carcinoma) (FIG. 6A-D). In glioma, it is clear that the methylation at cg17197774 may influence mda-9 expression ($R^2$=0.38; linear regression). In contrast, cg10129404 appears to have a negligible effect on mda-9 expression ($R^2$=0.051). Similar analysis was conducted for the TCGA KIRP dataset. Linear regression analyses indicate that the $R^2$ value for the plot of mda-9 expression vs. cg17197774 methylation is 0.25, while that of mda-9 expression vs. cg10129404 is almost zero. Overall, these analyses indicate that cg10129404's influence on mda-9 expression is unlikely.

Glioma

Figure 8B:
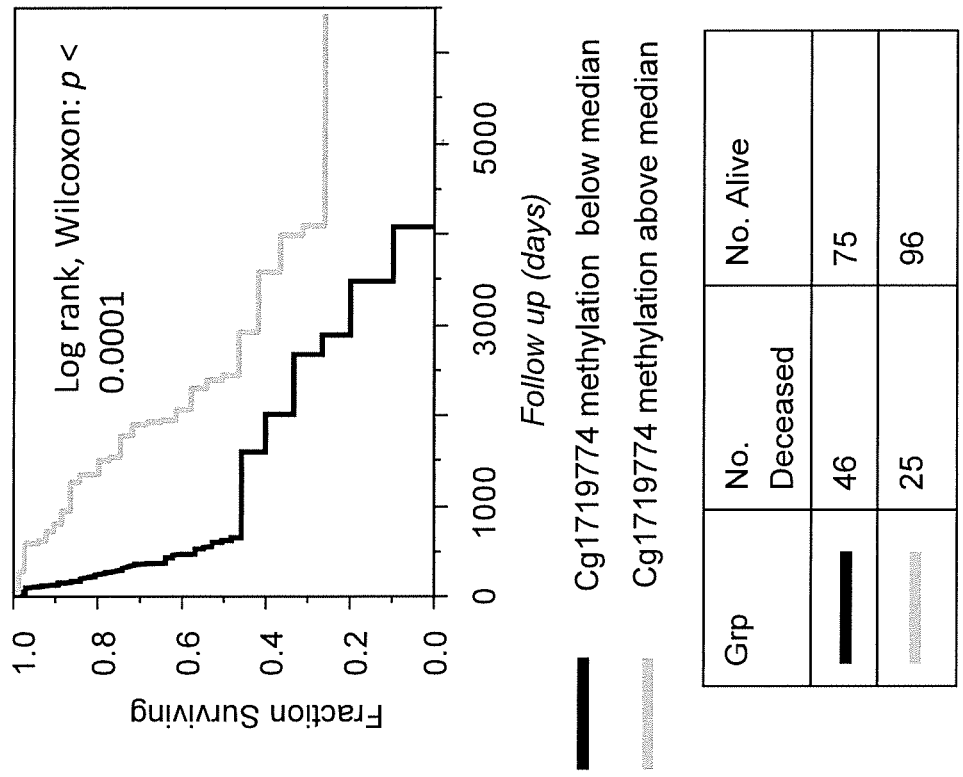
FIGS. 8A and B. Methylation at cg17197774 is a marker of clinical outcome in glioma. Patients were grouped into two, according to % methylation (A), or methylation value (Beta value) relative to median (B).
Figure 8A:
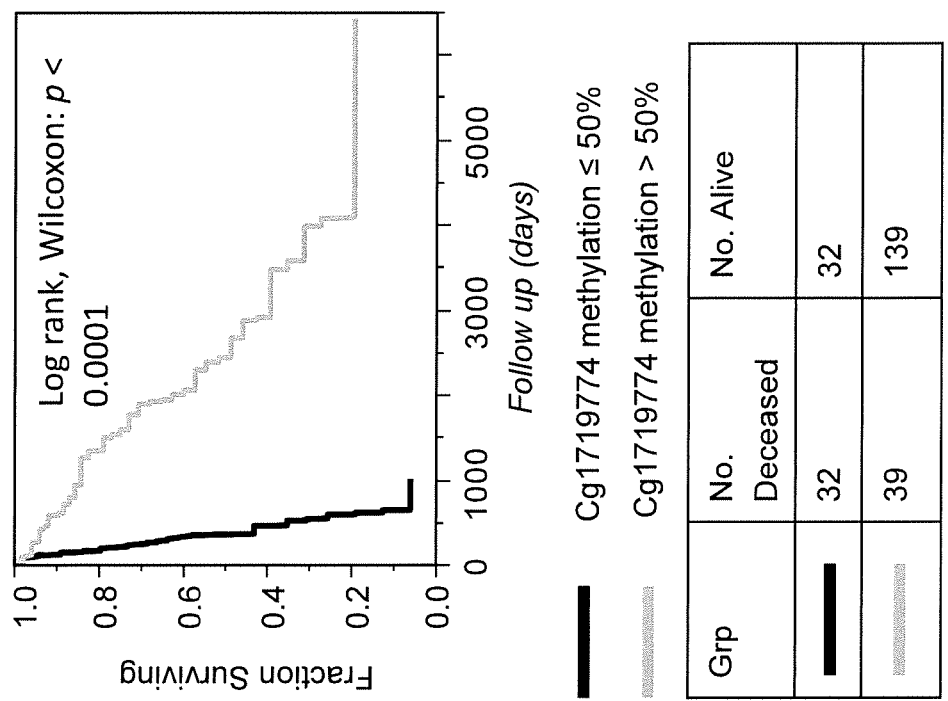

Having established that mda-9 expression correlates with methylation at cg17197774, the next step was to analyze the dual contribution of both methylation and copy number in mda-9 expression for each of the 6 datasets included in this study. The relationships between mda-9 expression, copy number and the methylation status of cg17197774 are illustrated in FIG. 7A-F. For glioma (whose mda-9 copy number is mostly neutral), we can see the effect of both copy number and methylation status. Copy number is a likely factor (R=0.26; expression vs. copy number). However, it is also clear that among the samples with only two copies of mda-9, those with low degree of methylation at the cg17197774 tend to have a higher mda-9 expression level (R=−0.61; expression vs. cg17197774 beta value). By itself, it appears that cg17197774 methylation status may be a reliable marker of survival in glioma (FIGS. 8A and B).

Melanoma, Prostate Cancer, Liver Hepatocellular Carcinoma and Kidney Renal Papillary Carcinoma.

On average, SKCM samples have the lowest beta values for cg17197774, at −0.295 (see Table 3 below). This may also explain why among the six TCGA cancer datasets, SKCM tumors have the highest expression levels for mda-9 (at more than 20,000 units; inv log 2 scale). Nonetheless, the influence of both factors is evident (correlation coefficients of −0.35 and 0.58 for expression vs. methylation and expression vs. copy number, respectively). The tumor sample with the highest overall mda-9 expression level (at more than 190,000 units) has an mda-9 copy number estimate of 25 and cg17197774 beta value of −0.45. For the TCGA COAD (colon adenocarcinoma), both copy number and cg17197774 methylation appear to factor in mda-9 expression, with the former (R=0.47) having greater influence than the latter (−0.22). A great majority of KIRP samples have a neutral copy number (CN=2) at the mda-9 locus. Not surprisingly, the elevated mda-9 expression is primarily due to hypomethylation at cg17197774 (mda-9 expression vs. cg17197774 methylation correlation coefficient=−0.5). In contrast to KIRP, the mode of mda-9 dysregulation in prostate cancer samples is primarily through copy number gain (R=0.67), with cg17197774 methylation apparently lacking any effect on the gene's expression level. Among LIHC primary tumors, it is clear that both copy number (R=0.55) and cg17197774 methylation (R=−0.45) are factors influencing mda-9 RNA levels.

Combination of the Six Cancer Datasets.

Figure 9A:
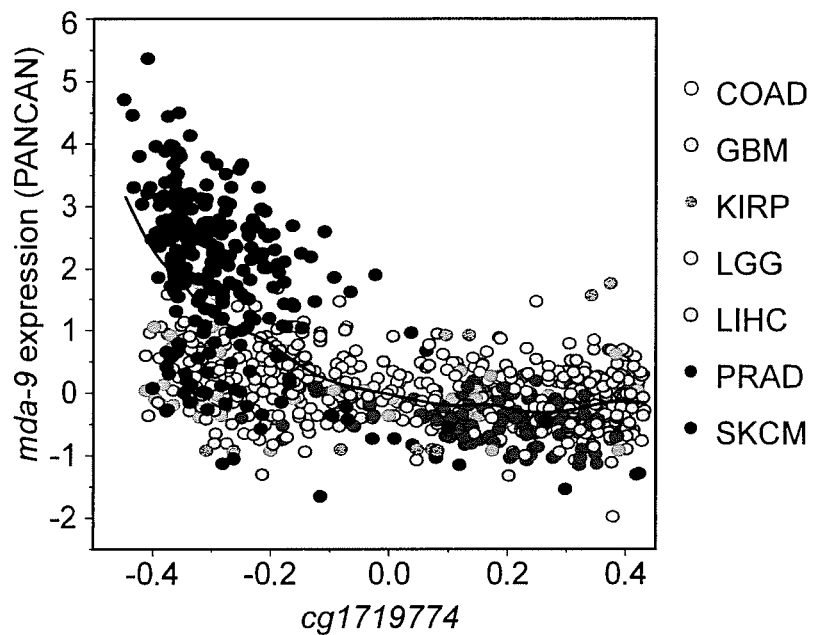
FIG. 9A-D. mda-9 expression (PANCAN-normalized) vs. cg17197774 Beta values with data points labeled according to TCGA cohort (A), and copy number (B). C. The same dataset with the exponential 3P regression plot. D. mda-9 expression vs. Copy Number, with data points marked according to cg17197774 Beta value.
Figure 9B:
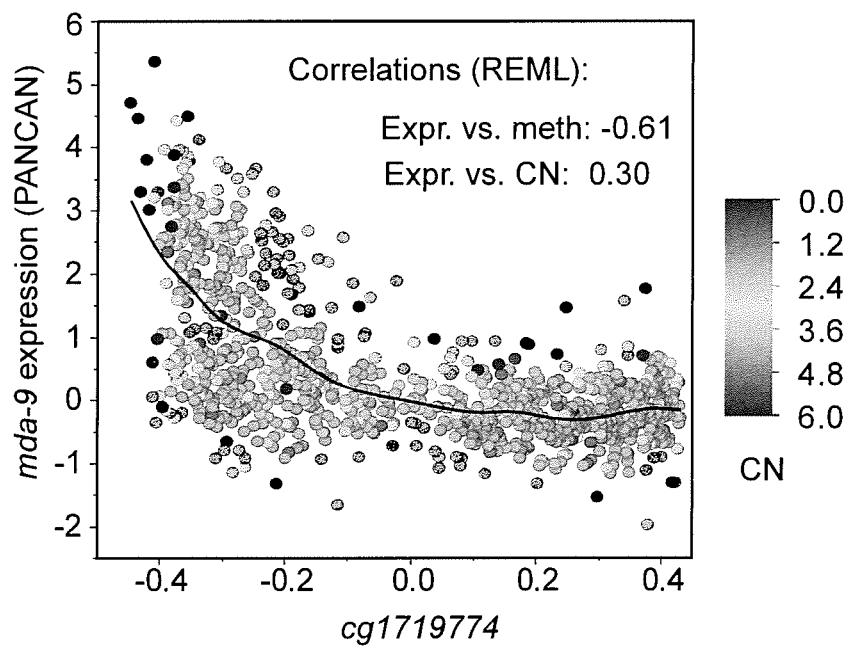
Figure 9C:
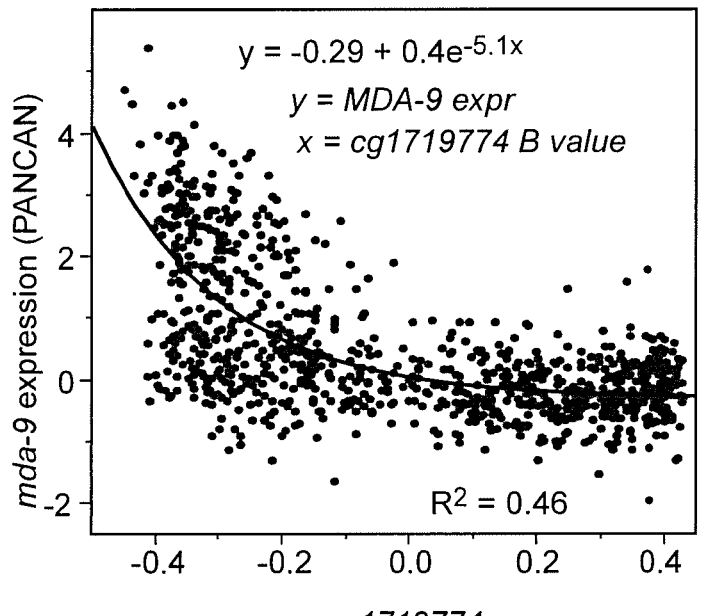
Figure 9D:
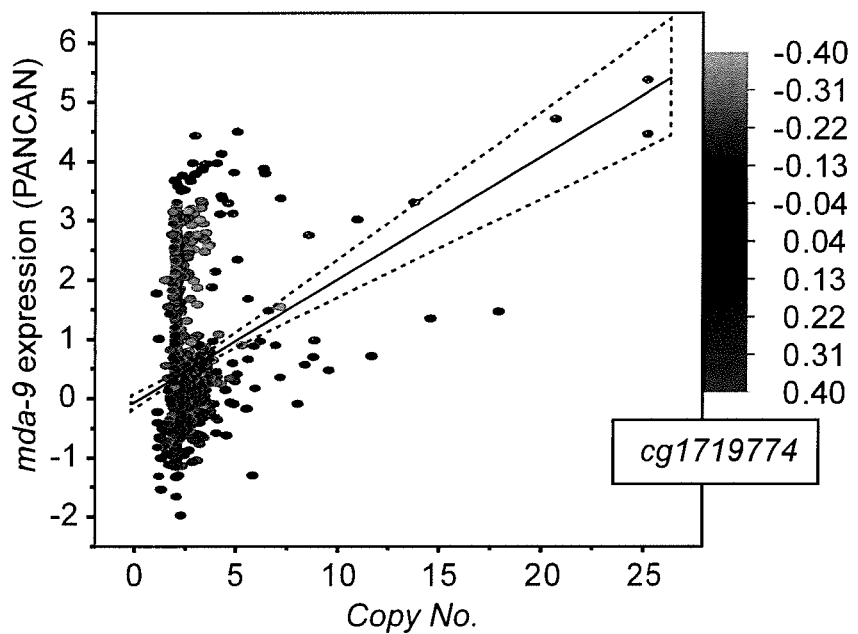

For a unified view on the effects of both copy number and cg17197774 methylation on mda-9 expression, we used the PANCAN-normalized expression value for mda-9. The PANCAN dataset is the merging of all the 22 TCGA RNASeq datasets (Chang, et al., 2013). According to the information provided by the UCSC Cancer Genomics Browser, the original level 3 RNASeq V2 datasets were downloaded from TCGA, log (base 2) transformed, then mean-normalized across all the cohorts. The normalization across all the cohorts provides more reliable relative values for gene expression. FIGS. 9 A-B show the same Cartesian plot (i.e. PANCAN-normalized mda-9 expression value vs. methylation at cg17197774) with varying information for each data point. As these figures indicate, there is a clear inverse exponential relationship between the two variables. As discussed previously, the highest mda-9 expression levels were those of SKCM samples, owing to the low beta values for cg17197774. The effect of copy number on mda-9 expression is illustrated in that those samples whose mda-9 copy number is 6 or higher mostly appear in the upper edges of the graph. This indicates that copy number can elevate mda-9 expression levels irrespective of the methylation status of cg17197774. Overall, the correlation coefficients (Multivariate REML statistics) for expression vs. methylation and expression vs. copy number are −0.61 and 0.30, respectively. This shows that the methylation status of cg17197774 has greater influence (compared to mda-9 copy number) towards the gene's expression level. FIG. 9C shows a superimposed exponential regression model (JMP Pro 10) relating mda-9 expression and cg17197774. Lastly, FIG. 9D illustrates the relationship between mda-9 expression and copy number. At this point, we already know that tumor samples with neutral copy number for mda-9 can have an elevated expression of the gene if it is hypomethylated at cg17197774.

mda-9 is Highly Expressed in Melanoma mda-9 RNA Expression Across all Cancer Types (PANCAN Dataset).

Figure 10A:
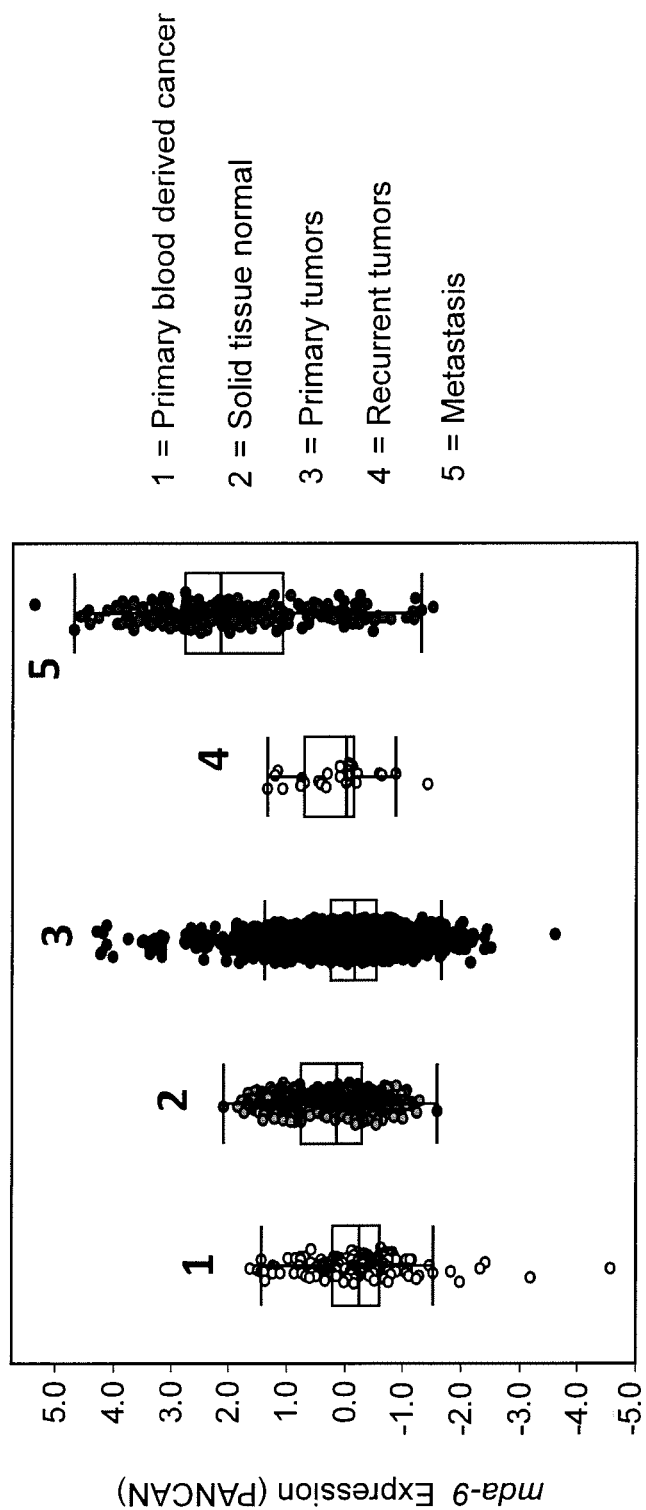
FIGS. 10A and B. The Expression of mda-9 (PANCAN-normalized) with samples grouped according to sample type (A) and TCGA cohort (solid normals not included (B). In B, the cohorts are the following: a. Acute Myeloid Leukemia [LAML], b. Bladder Urothelial Carcinoma [BLCA], c. Breast invasive carcinoma [BRCA], d. Cervical squamous cell carcinoma and endocervical adenocarcinoma [CESC], e. Colon adenocarcinoma [COAD], f. Uterine Corpus Endometrial Carcinoma [UCEC], g. Glioblastoma multiforme [GBM], h. Head and Neck squamous cell carcinoma [HNSC], i. Kidney Chromophobe [KICH], j. Kidney renal clear cell carcinoma [KIRC], k. Kidney renal papillary cell carcinoma [KIRP], l. Liver hepatocellular carcinoma [LIHC], m. Brain Lower Grade Glioma [LGG], n. Lung adenocarcinoma [LUAD], o. Lung squamous cell carcinoma [LUSC], p. Skin Cutaneous Melanoma [SKCM], q. Ovarian serous cystadenocarcinoma [OV], r. Pancreatic adenocarcinoma [PARD], s. Prostate adenocarcinoma [PRAD], t. Rectum adenocarcinoma [READ], u. Sarcoma [SARC], v. Thyroid carcinoma [THCA].
Figure 10B:
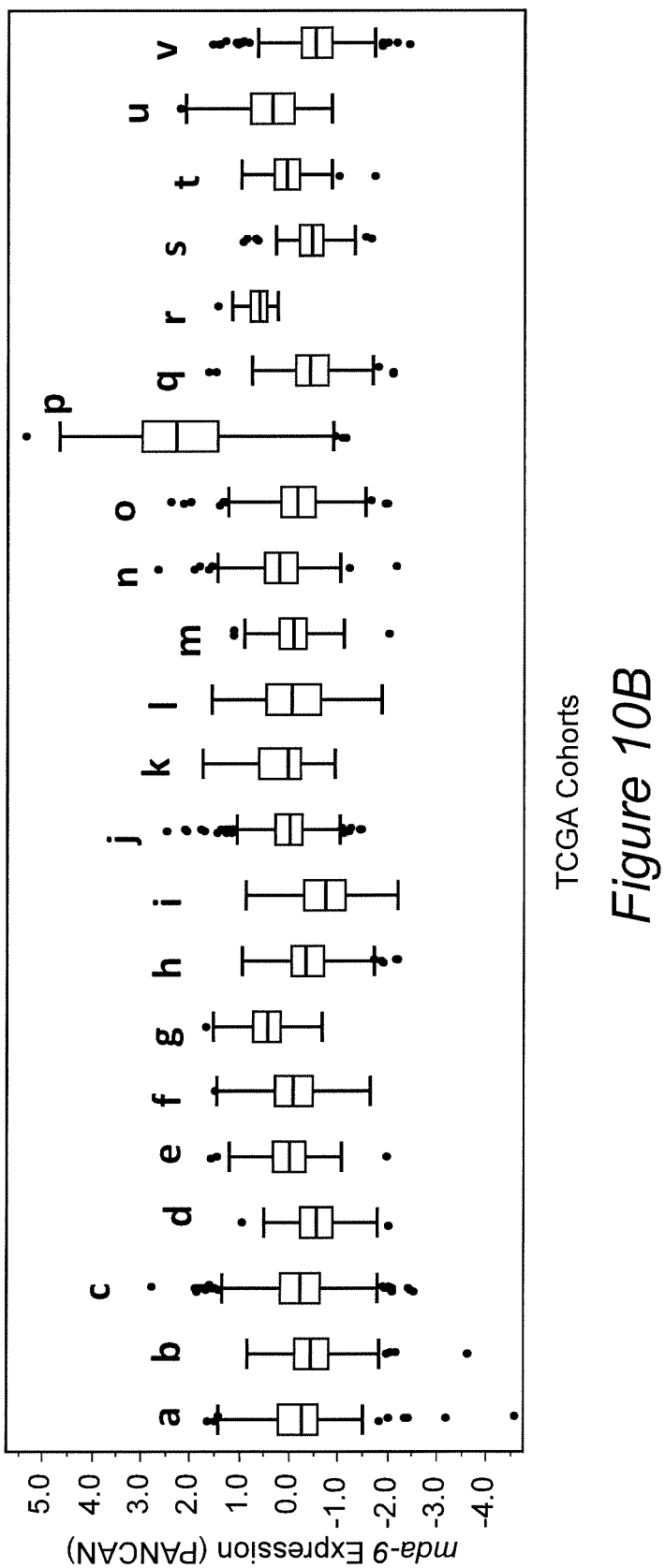

The results illustrated above point to mda-9 being most highly expressed in melanoma (among the 6 cancer types analyzed). We then proceeded to examine mda-9 expression in all of the TCGA cohorts through analysis of the TCGA PANCAN dataset. Covering 22 cancer types, the dataset includes 6040 samples (4982 primary tumors, 271 metastatic, 27 recurrent tumors, 173 peripheral blood, 587 solid tissue normals). First, the 6040 samples were grouped according to TCGA-defined sample types. On average, the highest mda-9 levels were those of metastasis samples, which were largely the melanoma (SKCM) samples (FIG. 10A). When mda-9 expression was divided according to cohort (without the normals), it is clear that mda-9 is most elevated in melanoma samples (FIG. 10B).

MDA-9 Protein Expression Across all Cancer Types (the Human Protein Atlas).

Figure 11A:
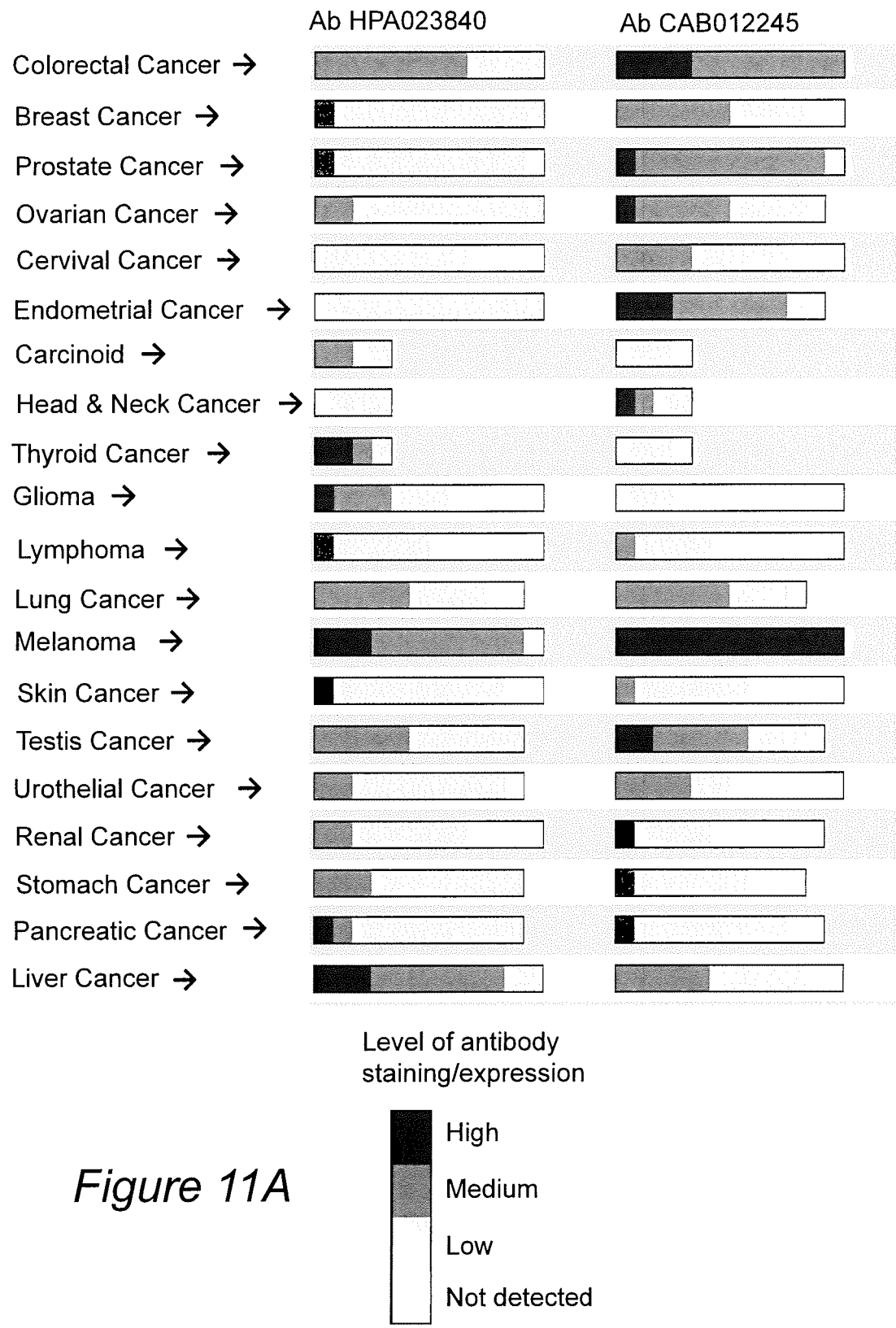
FIGS. 11A and B. A, MDA-9 protein levels, as assessed by Immunohistochemistry (semi-quantitative) using two different antibodies. The bars indicate that melanoma has the highest MDA-9 expression among different cancer types. B, immunohistochemical images of melanoma and glioma sections, indicative of the former's stronger MDA-9 signal.
Figure 11B:
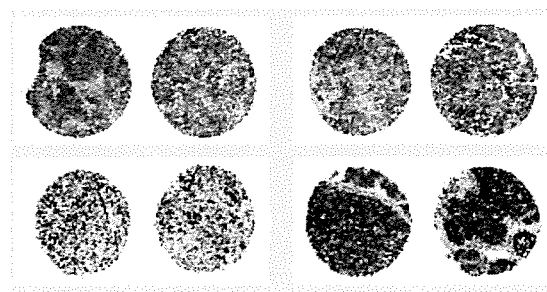
Figure 11B:
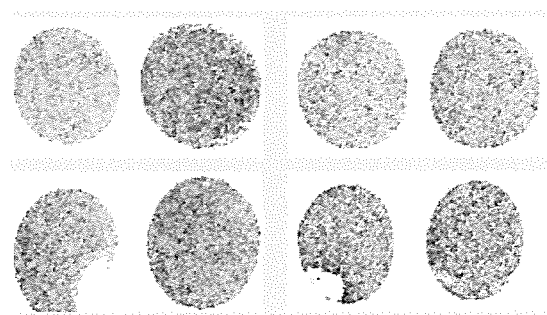
Figure 12A:
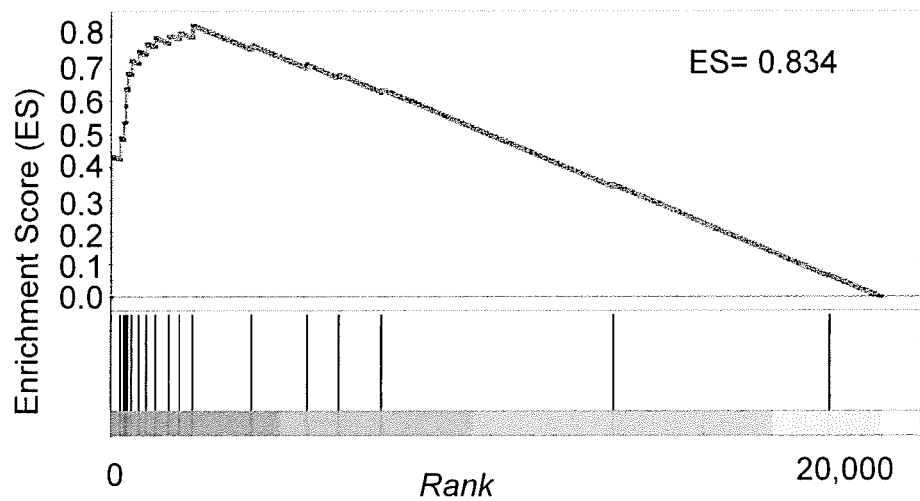
FIG. 12A-D. Four representative pathways and processes, which exhibited gene enrichment in GSEA analysis. Indicated are the core enrichment genes in order of decreasing rank. A, interleukin receptor activity; B, complement cascade; C, regulation of IGF activity by IGFBPs; D, VEGF signaling.
Figure 12B:
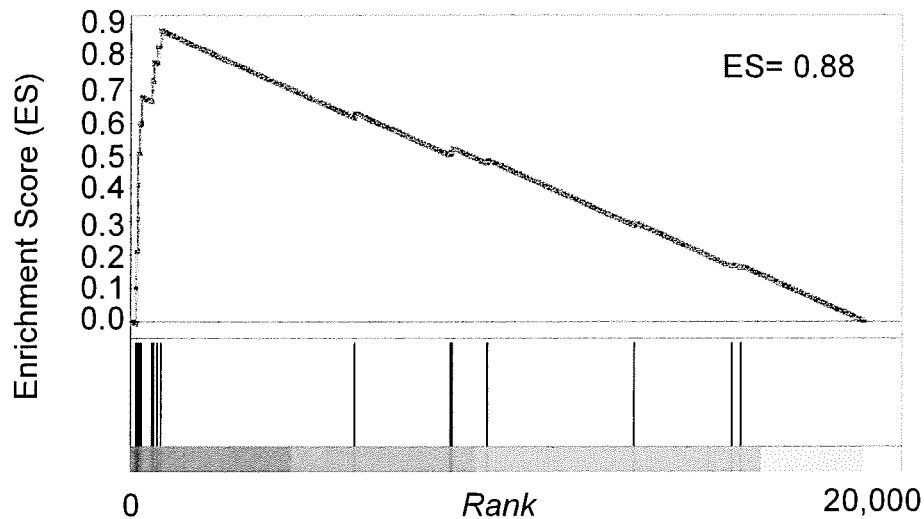
Figure 12C:
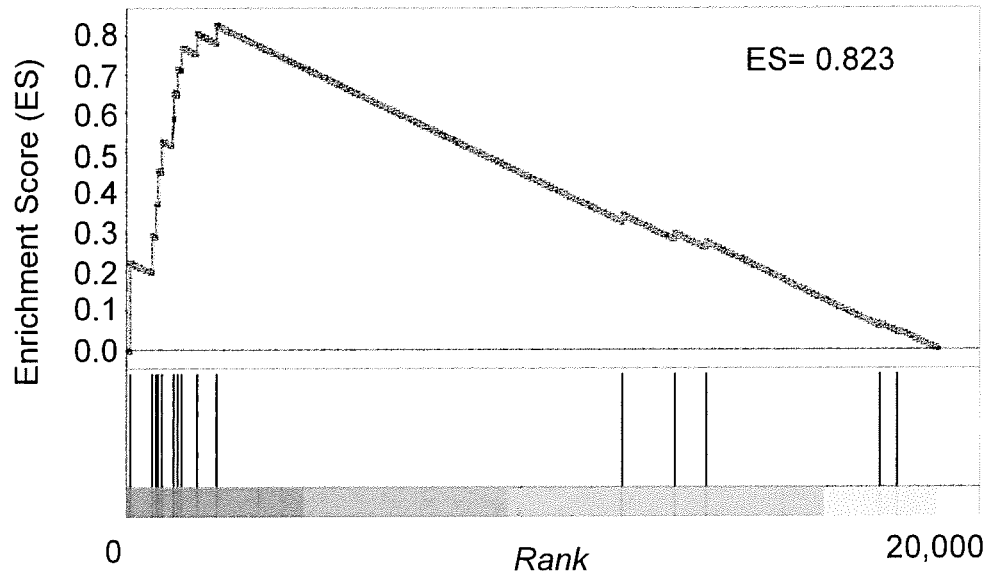
Figure 12D:
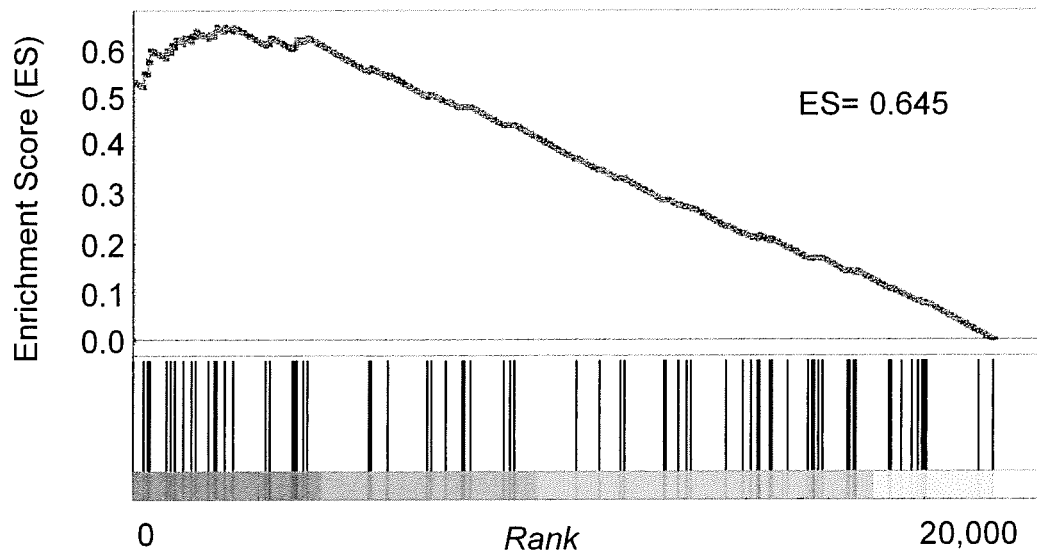

TCGA also has datasets for protein expression (using Reverse Phase Protein Array). However, it only covers a few hundred select proteins (the most widely studied cancer-related genes) and does not include MDA-9. However, a very comprehensive source of genome-wide protein expression is the Human Protein (www.proteinatlas.org/) where proteins were immunohistochemically analyzed in different cancer types. For MDA-9, two different antibodies were used: HPA023840 from Sigma-Aldrich and CAB012245 from Abcam. Consistent with results from the PANCAN analysis, MDA-9 according to Human Protein Atlas, is most highly expressed in melanoma (See FIG. 11A). In particular, the HPA023840 signal was much stronger in melanoma compared to glioma (FIG. 11B). The staining results were evaluated by a trained pathologist, who assigned intensity (negative, weak, moderate or strong), fraction of stained cells (rare, <25%, 25-75% or >75%), as well as subcellular localization (nuclear and/or cytoplasmic/membranous). A summary of the information regarding MDA-9 protein levels in six cancer types (whose TCGA cohorts are included in this report), are included in Table 3.

TABLE 3

Comparison of mda-9 copy number, CpG methylation (at cg17197774), RNA level and protein level in six TCGA cohorts (cancer samples only). The protein analysis data (semi-quantitative) were taken from the Human Protein Atlas.

| Tumor Cohort (TCGA) | No. of tumor samples | Copy number estimate (lowest, highest) | CpG Methylation at cg17197774 (−0.5 to 0.5; low to high) | Expression level |
|---|---|---|---|---|
| SKCM | 241 | 2.80 (1.15, 24.2) | −0.295 | 23062 ± 20569 |
| PRAD | 175 | 2.18 (1.20, 8.82) | 0.195 | 3039 ± 943 |
| COAD | 188 | 2.82 (1.11, 17.93) | −0.019 | 4172 ± 1514 |
| GBM/LGG | 257 | 2.09 (1.09, 5.56) | 0.209 | 4308 ± 1500 |
| LIHC | 68 | 2.92 (1.09, 14.55) | −0.088 | 4623 ± 2505 |
| KIRP | 60 | 2.16 (0.84) | −0.014 | 5553 ± 3268 |

Predicting Genes and Pathways Associated with mda-9 Dysregulation in Glioma

Comparing mda-9 High and mda-9 Low Subtypes of Glioma.

Genome-wide expression datasets are also be useful in predicting genes or pathways associated with mda-9 dysregulation. Our approach was to start with the isolation of two subsets (out of the complete cohort of tumor samples) at the opposite tail ends of distribution in terms of mda-9 expression: a) mda-9-high, i.e. those whose mda-9 expression levels are at least 1 standard deviation higher than the average, and b) mda-9-low, i.e. those cases whose mda-9 expression levels are at least 1 standard deviation lower than the average. The comparative genome-wide expression of these two subsets was then examined to identify the genes, functionalities and molecular pathways, which are most likely associated with mda-9 upregulation or mda-9 downregulation. This approach is referred to as "Virtual Gene Over-expression or Repression" or VIGOR. Genes were then ranked according to a comparative statistic (either signal-to-noise ratio or fold-change) between the two groups. The VIGOR approach was applied to the two glioma datasets (TCGA and GSE4290) and the results (not shown) were highly concordant. The resulting signal-to-noise ratios (for all genes) in the TCGA glioma dataset directly correlate with those of the GSE4290 dataset.

Another statistical tool employed is the Gene Set Enrichment Analysis (GSEA) available through the Broad Institute (www.broadinstitute.org/gsea/) (Subramanian, et al., 2005). GSEA analysis starts with the recognition that genes are associated with particular groups (or gene sets), such as pathways defined in Reactome, Biocarta, or KEGG databases, as well as molecular functions, biological processes and subcellular locations according to Gene Ontology. GSEA then examines the collective trends of how genes belonging to a particular gene set behave through the calculation of an Enrichment Score (ES). A high concentration of highly ranked genes (rank=1 for the gene with the highest fold-change; mda-9 high/mda-9 low) belonging to a particular gene set translates to an ES value close to 1, which may be interpreted as that gene set being likely associated with mda-9 upregulation. An ES value close to −1 for a gene set is interpreted as that gene set being associated with mda-9 downregulation.

Genes that are Most Highly Dysregulated in mda-9-High Glioma.

When the top 300 up-regulated genes were overlapped against the MSigDB database (www.broadinstitute.org/gsea/msigdb), it was revealed that the list includes 29 cytokines and growth factors, 34 transcription factors, 29 transcription factors which are also homeodomain proteins, 23 cell differentiation markers, 9 oncogenes and 1 protein kinase. On the other hand, when the top 300 down-regulated genes were overlapped against the same database, we found that only 5 were classified as cytokines and growth factors, 16 as transcription factors, 3 as homeodomain transcription factors, 2 cell differentiation markers, 1 oncogene (RANBP17) and 8 as protein kinases.

These results provided us with information as to the type of genes directly associated with mda-9 expression. They are likely involved in cell proliferation, or more precisely in the advancement of glioma carcinogenesis. Among the top 100 upregulated genes are LTF (lactotransferrin), CHI3L1/L2 (cartilage glycoproteins), PLA2G2A (phospholipase A2, group IIA), POSTN (periostin, osteoblast specific factor), ABCC3 (ATP-binding cassette, sub family C (CFTR/MRP), SAA1 (serum amyloid A1), various ILs (interleukins) and ILRs (interleukin receptors), IBSP (integrin-binding sialoprotein), MMPs (matrix metallopeptidases), TIMPs (TIMP metallopeptidase inhibitors), COLs (collagens), HOXs (homeobox genes) and the scavenger receptor CD163. None of the genes in the top list are in the 8q arm, which means that the VIGOR approach minimized the copy number effect in gene selection. Among the most down-regulated genes are GRIN1 (glutamate receptor, ionotropic, N-methyl D-aspartate 1), CUX2 (cut-like homeobox 2), INA (internexin neuronal intermediate filament protein, alpha), SVOP (SV2 related protein homolog) and CHGA (chromogranin A (parathyroid secretory protein 1)). The MMPs, TIMPs, COLs and IBSP are all components of extracellular matrix processes crucial to cell invasion and metastasis, thus, these genes' connections to mda-9 are quite clear.

Pathways and Gene Groups Identified Through GSEA.

Instead of inspecting the likely mda-9 associated genes by inspecting them one at a time as above, GSEA analysis was able to identify the groups of genes representing molecular pathways and related functionalities.

a) Association with Extracellular Matrix (ECM), Cell Adhesion, and Migration a-1. The Metallopeptides and Associated Proteins.

Among the gene sets exhibiting the highest ES values are those related to the extracellular matrix. These include gene groups such as Reactome's degradation of extracellular matrix (ES=0.79), GO Molecular Function's metallopeptidase activity (ES=0.84) and GO Cellular Component's extracellular matrix (ES=0.77) All of these gene sets essentially refer to the same group of genes, which include the matrix metallopeptidases (MMPs) and its activator proteins (TIMPs). MMPs are zinc and calcium dependent proteases, which upon secretion can degrade the extracellular matrix, an essential process for the cells to accomplish invasion and metastasis. 12 genes are considered as part of core enrichment. These include MMP9 and TIMP1, which were up-regulated (mda-9 high vs. mda-9 low) 44-fold and 27-fold, respectively, as well as MMP13, MMP1, TIMP1, MMP11, MMP9 and TPSAB1 (tryptase alpha/beta 1). These are mostly associated with degradation of the glycoproteins fibrillin, fibronectin and decorin.

a-2. Collagens.

Various collagen genes also registered over-expression among mda-9-high gliomas and this is reflected in the ES values for various gene sets such as Reactome's collagen formation (ES=0.78). The following genes are highly-expressed in mda-9-high tumors: Type I (COL1A2, COL1A1), Type III (COL3A1), Type IV (COL4A1, COL4A2), Type V (COL5A1, COL5A2), Type VI (COL6A3, COL6A2, COL6A1), Type VIII (COL8A1, COL8A2), Type XII (COL12A1), Type XIII (COL13A1), Type XIV (COL14A1) and Type XV (COL15A1). Other related genes up-regulated in mda-9 high tumors are PCOLCE (procollagen C-endopeptidase enhancer) and the chaperone protein SERPINH1 [serpin peptidase inhibitor, clade H (heat shock protein 47), member 1, (collagen binding protein 1)]. Collagen fibers provide the network of roads which cells travel on during migration.

a-3. Integrins and Focal Adhesion Genes.

Other ECM-related gene sets highly enriched in mda-9 High glioma belong to the following categories: Reactome's integrin cell surface interactions and KEGG's focal adhesion. Among the components of these sets are genes coding for various collagen molecules (COL1A2, COL1A1, COL4A1, COL4A2), integrins (ITGA4, ITGA5, ITGB3, ITGB2), IBSP (integrin-binding sialoprotein), the adhesive glycoprotein THBS1 (thrombospondin 1), the cell surface glycoprotein ICAM1 (intercellular adhesion molecule 1), laminins (LAMB1, LAMC1) and fibronectin (FN1). There were recent reports indicating that mda-9 is indeed involved in the activation of focal adhesion kinase (FAK). MDA-9's role in the activation of FAK has been demonstrated in breast cancer cells (through the crosstalk between Protein Kinase C α and MDA-9) dendritic cells and glioma (through FAK-JNK and FAK-AKT signaling). MDA-9 was also shown to positively regulate the scaffold function of ILK (integrin-linked kinase), part of KEGG's focal adhesion gene set, which is also up-regulated in mda-9 High glioma.

a-4. Neurite Outgrowth.

The Reactome gene set centered around NCAM (neural cell adhesion molecule), important for neurite outgrowth (ES=0.76), was also enriched among mda-9 High glioma samples. NCAM, a member of the immunoglobulin (Ig) superfamily, is a mediator of the neurite outgrowth process. In glioma cells, it was shown that neurite outgrowth can be promoted through a cadherin-dependent adhesion The computational prediction of MDA-9's association with the neurite outgrowth process was primarily driven by the overexpression of various collagen genes (e.g. COL6A3, COL3A1, COL1A2, COL1A1, COL6A2, COL5A1) among mda-9 High glioma. Another important gene in the neurite outgrowth process is ST8SIA4 (ST8 alpha-N-acetyl-neuraminide alpha-2, 8-sialyltransferase 4), an enzyme necessary for synthesis of polysialic acid, which modulates NCAM1's adhesive properties. The gene is also highly up-regulated in mda-9 High tumors.

b) Association with Immuno Signaling Pathways b-1. Interleukins.

Among the most highly up-regulated genes in mda-9 High gliomas are, IL8 (interleukin 8) (19-fold), and IL2RA (interleukin 2 receptor, alpha) (21-fold). Indeed, GSEA analysis identifies a number of IL-related gene sets directly correlating with mda-9 up-regulation. These include the following: Biocarta gene sets belonging to the IL17 Pathway (ES=0.85), Inflammation Pathway (ES=0.78), IL2 pathway (ES=0.74), IL7 pathway (ES=0.73) and IL12 pathways (ES=0.70); GO Molecular Function gene sets involving interleukin receptor activity (0.83) and interleukin binding (0.79). The upregulation of many IL-related genes and pathways is likely related to the glioma cells trying to maintain their immunosuppressive state as much as possible. The involvement of mda-9 in these processes has been verified in a number of reports. Another interleukin (IL16), which contains 4 PDZ domains, may interact with MDA-9. An earlier report suggested that tumor necrosis factor-alpha (TNFα) is capable of up-regulating the expression of both IL8 and mda-9 in endothelial cells.

b-2. Interferon.

Many genes involved in the IFN-γ pathway were found to be up-regulated in mda-9 High gliomas as shown in the GSEA plot for Reactome's IFN-γ pathway gene set (ES=0.73). These include the following: major histocompatibility complex class II genes (HLA-DQA1, HLA-DQA2, HLA-DRB1, HLA-DRB5), guanylate binding proteins (GBP5, GBP1, GBP2), CD44, the nuclear antigen SP100, suppressor of cytokine signaling (SOCS3, SOCS1) and interferon gamma (IFNG). The top gene on the list (most highly up-regulated in mda-9 High glioma) is GBP5, proven to be up-regulated by IFN-γ induction b-3. CTLA4 Pathway.

Also noticeable is the apparent activation of the CTLA4 pathway among mda-9 High glioma. CTLA4 (fold change ~3) is a receptor on the surface of Helper T Cells, which can down-regulate the immune system. Other mda-9 High up-regulated genes belonging to Biocarta's CTLA4 Pathway gene set (ES=0.86) are genes coding for proteins that form a complex with T cell receptors (CD3D, CD3E), lymphocyte-specific protein tyrosine kinase (LCK), proteins forming the MHC Class II complex (HLA-D3A, HLA-DRB1), IL2-inducible T-cell kinase (ITK), inducible T-cell co-stimulator (ICOS) and membrane-bound proteins necessary for T cell activation (CD80, CD86). The identification of these genes is consistent with the knowledge of the presence of infiltrating cells in the glioma environment.

b-4. Complement Cascade.

The complement cascade is another pathway found to be heavily dysregulated among glioma samples with elevated MDA-9. As demonstrated by GSEA plots for complement cascade-related gene sets in both Reactome (ES=0.84) and Biocarta (ES=0.88), the complement component genes CFB, CFD, C6, C7, C1S, C1R, C2, C1QA, CR1, C4BPA are among the most highly up-regulated genes in the MDA-9-high glioma subset.

c) Association with Transcriptional Activation and Other Signaling Pathways c-1. IGF Signaling.

The GSEA analysis indicated that there is a significant dysregulation of the Reactome gene set "regulation of insulin like growth factor IGF activity by insulin like growth factor binding proteins IGFBPs", among the MDA-9-high glioma group (ES=0.82). The most highly ranked genes in this gene set include IGF binding proteins (IGFBPs (1-5)), matrix metallopeptidases (MMP1, MMP2), cathepsin (CTSG), pappalysin 2 (PAPPA2) and vascular endothelial growth factor A (VEGFA). IGFBPs serve as modulators of IGF1/2, whose downstream transcriptional targets are pro-invasion genes such as MMP2 and VEGFA. On the other hand, PAPPA2 and CTSG are proteases, which regulate IGFBPs.

IGFBP2 in Particular Proved to be a Promoter of Glioma Progression c-2. VEGF Pathway.

VEGFA is highly up-regulated in the glioma subset with elevated MDA-9 expression. The VEGF signaling pathway (KEGG) gene set is indeed enriched among MDA-9 high gliomas, according to results from the GSEA analysis (ES=0.65). Aside from VEGFA, other highly ranked genes belonging to the gene set are several of its downstream targets including: the phospholipase genes PLA2G2A, PLG2G5 and PLG2G4A; the adaptor protein SH2D2A (SH2 domain containing 2A, or VRAF); the RAS-related gene RAC2; prostaglandin-endoperoxide synthase 2 (PTGS2 or COX-2) and the phosphatidylinositol-4,5-bisphosphate 3-kinase genes PIK3CG (catalytic) and PIK3R5 (regulatory). FIGS. 12A-D further illustrate these finding.

e) Pathways Directly Associated with mda-9 Down-Regulation

For the mda-9 Low subgroup, only two gene sets exhibited ES and FDR q values within the acceptable range. One is the Reactome gene set GABA-A receptor activation, which has ES and FDR q values of −0.88 and 0.005 respectively. The other one is the Reactome gene set GABA synthesis release uptake and degradation (ES=−0.64, FDR q=0.084). For the first gene set, the core enrichment genes (i.e. those which are highly down-regulated in mda-9 High glioma) include various GABA-A receptor genes (GABRG3, GABRB1, GABRA6, GABRA2, GABRA3, GABRA4, GABRG3, GABRA5, GABRG2, GABRA1 and GABRB2). For the other gene set, the genes most likely to influence the pathway are SNAP25 (synaptosomal-associated protein, 25 kDa), SYT1 (synaptotagmin 1), SLC32A1 [solute carrier family 32 (GABA vesicular transporter), member 1], glutamate decarboxylase genes (GAD2, GAD1), RIMS (regulating synaptic membrane exocytosis 1) and STXIA [syntaxin 1A (brain)].

Summary

Through the integrated bioinformatic analyses of publicly available cancer genomic datasets, we were able to comprehensively analyze epigenetic and molecular factors associated with the dysregulation of mda-9 in various types of cancer. We found that the elevation of mda-9 expression during cancer progression correlates with both a copy number increase and reduced methylation at a key CpG site (cg17197774) located at the intron, more than 1,000 bases 3' from the CpG island. These observations derive from analyses of genome-wide expression, CpG methylation and copy number for TCGA Glioma (Glioblastoma Multiforme, Lower Grade Glioma), SKCM (Skin Cutaneous Melanoma), PRAD (Prostate Adenocarcinoma), COAD (colon adenocarcinoma), LIHC (Liver Hepatocellular Carcinoma) and KIRP (Kidney Renal Papillary Cell Carcinoma) datasets.

Methylation at cg17197774 thus serves as a prognostic marker in cancer, with hypomethylation correlating with an expectation of poor survival and a need for radical intervention. Further, elevated expression of mda-9, as well as the expression (or lack thereof) of proteins and protein groups and pathways identified herein, may be used in conjunction with and/or to confirm predictions made based on methylation at cg17197774.

Example 2. Prognosis and Treatment of a Solid Tumor: Case 1

A patient is diagnosed as having a solid tumor. A liquid biopsy is obtained and bisulfite-PCR analysis is performed to determine the level of methylation at site cg17197774. The methylation level is expressed as a "score" on a scale of −0.5 to +0.5, with −0.5 indicating a high grade tumor with a high probability of metastasis. The score is −0.4. The patient is immediately treated aggressively. The treatment includes surgery, radiation therapy and chemotherapy, followed by adjuvant immunotherapy.

Example 3. Monitoring Treatment

The treatment of the patient described in Example 2 is monitored by determining the level of cg17197774 methylation in a liquid biopsy after surgery, before, during and after each of radiation therapy, chemotherapy, and adjuvant therapy, or before, during and after combinations of these. After a first round of chemotherapy is administered, the cg17197774 methylation level of cells in the liquid biopsy is measured and the results show that the level is the same. A different chemotherapeutic agent is administered and tests showed that the level of cg17197774 methylation of cells in the liquid biopsy decreases to normal levels. No further chemotherapy is administered.

Example 4. Prognosis and Treatment of a Solid Tumor: Case 2

A patient is diagnosed as having a solid tumor. A liquid biopsy is obtained and bisulfite-PCR analysis is performed to determine the level of methylation at site cg17197774. The methylation level is expressed as a "score" on a scale of −0.5 to +0.5, with −0.5 indicating a high grade tumor with a high probability of metastasis. The score is +0.4. The patient is not treated immediately; rather, the physician undertakes "watchful waiting" during which the size and cg17197774 methylation status of the tumor are monitored. If the methylation level remains stable or increases, no further action is taken. If the methylation level decreases, the tumor is removed and a moderate course of chemotherapy is administered.

REFERENCES (2011). PLoS Biol 9, e1001046.
Bettum, I. J et al. (2014). Cancer Lett 344, 28-39.
Chandran, U. R et al. (2007). BMC Cancer 7, 64.
Chang, K., et al. (2013). Nat Genet 45, 1113-20.
Ernst, J et al. (2011). Nature 473, 43-9.
Goldman, M et al. (2013). Nucleic Acids Res 41, D949-54.
Joshi-Tope, G., et al. (2005). Nucleic Acids Res 33, D428-32.
Kaiser, J. (2005). Science 307, 1182.
Kim, H. J., et al. (2009). Am J Surg Pathol 33, 1276-86.
Mermel, C. H et al. (2011). Genome Biol 12, R41.
Sandoval, J., et al. (2011). Epigenetics 6, 692-702.
Ponten, F. et al. (2012). PLoS One 7, e37041.
Subramanian, A. et al. (2005). Proc Natl Acad Sci USA 102, 15545-50.
Sun, L et al. (2006). Cancer Cell 9, 287-300.
Talantov, D. et al. (2005). Clin Cancer Res 11, 7234-42.
Uhlen, M. et al. (2010). Nat Biotechnol 28, 1248-50.
Zhu, J et al. (2009). Nat Methods 6, 239-40.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating cancer in a subject in need thereof, comprising
   i) measuring a level of CpG methylation at cg17197774 in a tumor sample from the subject; and
   ii) detecting a level of CpG methylation below a reference value; and
   (iii) treating the subject with one or more of surgical debulking, chemotherapy, radiation therapy, or adjunct immunotherapy; wherein one or more of dose, frequency, and duration of treatment is greater than indicated for a subject having a level of tumor CpG methylation at cg17197774 above the reference value.

2. The method of claim 1, further comprising measuring, in the tumor sample from the subject, one or more of
   i) a level of MDA-9/Syntenin protein expression;
   ii) a level of expression of one or more downstream marker genes activated by MDA-9/Syntenin, wherein the marker genes are selected from the group consisting of insulin Growth Factor Binding Protein-2 (IGFBP-2), disintegrin and metalloproteinase with thrombospondin, amyloid, precursor protein 770, HSP90 cochaperone CDC37, growth-regulated alpha protein (CXCL1), cysteine-rich 61/connective tissue growth factor/nephroblastoma 1 (CCN1), connective tissue growth factor 2 (CCN2), macrophage migration inhibitory factor, urokinase-type plasminogen activator, isoform 12 of CD44 antigen, agrin, long isoform of laminin subunit gamma-2, and isoform 1 of connective tissue growth factor; and
   iii) a copy number of mda-9/Syntenin.

3. The method of claim 1, wherein the step of treating the subject comprises at least two, three or four of: surgical debulking, chemotherapy, radiation therapy, or adjunct immunotherapy.

4. A method of monitoring a cancer treatment in a subject in need thereof, comprising
   i) prior to beginning the cancer treatment, measuring a pre-treatment level of CpG methylation at site cg17197774 in a tumor sample from the subject,
   ii) administering the cancer treatment to the subject,
   iii) measuring a post-treatment level of CpG methylation at cg17197774; and
   iv) (a) if the post-treatment level of CpG methylation is higher than the pre-treatment level of CpG methylation, repeating the cancer treatment; or
   (b) if the post-treatment level of CpG methylation is the same as or lower than the pre-treatment level of CpG methylation, administering a different cancer treatment to the subject.

5. The method of claim 4, further comprising measuring, in the tumor sample from the subject, one or more of
   i) a level of MDA-9/Syntenin protein expression;
   ii) a level of expression of one or more downstream marker genes activated by MDA-9/Syntenin, wherein the marker genes are selected from the group consisting of insulin Growth Factor Binding Protein-2 (IGFBP-2), disintegrin and metalloproteinase with thrombospondin, amyloid, precursor protein 770, HSP90 cochaperone CDC37, growth-regulated alpha protein (CXCL1), cysteine-rich 61/connective tissue growth factor/nephroblastoma 1 (CCN1), connective tissue growth factor 2 (CCN2), macrophage migration inhibitory factor, urokinase-type plasminogen activator, isoform 12 of CD44 antigen, agrin, long isoform of laminin subunit gamma-2, and isoform 1 of connective tissue growth factor; and
   iii) a copy number of mda-9/Syntenin.

6. The method of claim 4, further comprising repeating steps ii) and iii) a plurality of times during a course of treatment and/or after the course of treatment is finished.

7. The method of claim 1, wherein the reference value is: a reference value from a control population of subjects with a high grade tumor prior to treatment; a reference value from a control population of subjects with a low grade tumor prior to treatment; a reference value from a control population of cancer-free subjects who have never been diagnosed with cancer; a reference value from a control population of subjects who have been diagnosed with and are being treated for cancer; a reference value from a control population of cancer-free subjects who have previously been successfully treated for cancer; a reference value from a control population of subjects diagnosed with metastatic cancer, or a reference value from normal or tumor tissue from the subject.

8. The method of claim 1, wherein the cancer is selected from the group consisting of glioma, prostate cancer, melanoma, liver hepatocellular carcinoma, kidney papillary carcinoma, pancreatic carcinoma, breast carcinoma, bladder carcinoma and colon adenocarcinoma.

9. The method of claim 1, wherein the tumor sample is a liquid biopsy.

10. The method of claim 4, wherein the downstream marker genes are IGFBP-2 and urokinase-type plasminogen activator (uPA).

11. The method of claim 1, wherein treating the subject comprises surgical debulking and one or more of chemotherapy, radiation therapy, or adjunct immunotherapy.

* * * * *

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 1
gtgggtggca cggggcccgc gg                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 2
gcacggggcc cgcgggcacg aa                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 3
cccgcgggca cgaacagccg aa                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 4
cagcggacag cgggcggcat ga                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 5
cggcatgaac cgccccactt tg                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
cccactttgc cggatacctg ga                                              22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic oligonucleotide primer

<400> SEQUENCE: 7
gcctcggggg cggtcctcgg gc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
ggtcctcggg cgcgcaccgc tc                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 9
tcctcgggcg cgcaccgctc tc                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 10
gcatcctggt cgcagccgtt tt                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 11
tcccagtgct cggcgtttct ag                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 12
taatggttgc cggttaaatg ta                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 13
ttaaaattca cggcaccatg ga                                              22
```